United States Patent
Glock et al.

(10) Patent No.: US 7,915,199 B1
(45) Date of Patent: *Mar. 29, 2011

(54) HERBICIDAL COMPOSITION

(75) Inventors: Jutta Glock, Mumpf (CH); Adrian Alberto Friedmann, Reading (GB); Derek Cornes, Münchenstein (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 291 days.

This patent is subject to a terminal disclaimer.

(21) Appl. No.: 10/070,936

(22) PCT Filed: Sep. 5, 2000

(86) PCT No.: PCT/EP00/08658
§ 371 (c)(1),
(2), (4) Date: Aug. 9, 2002

(87) PCT Pub. No.: WO01/17351
PCT Pub. Date: Mar. 15, 2001

(30) Foreign Application Priority Data

Sep. 7, 1999 (CH) ........................ 1641/99

(51) Int. Cl.
*A01N 43/90* (2006.01)
*A01N 43/40* (2006.01)
*A01N 43/58* (2006.01)
*C07D 498/04* (2006.01)

(52) U.S. Cl. ........ 504/105; 504/106; 504/107; 504/110; 504/112; 504/218; 504/219; 504/220; 540/545

(58) Field of Classification Search ................. 504/132, 504/134, 136, 137, 139, 105, 106, 107, 110, 504/112, 218, 219, 220, 545; 540/545, 218
See application file for complete search history.

(56) References Cited

U.S. PATENT DOCUMENTS

| | | | | |
|---|---|---|---|---|
| 5,474,974 A | * | 12/1995 | Kruger et al. | 504/236 |
| 5,683,965 A | | 11/1997 | Bachmann et al. | |
| 5,985,797 A | * | 11/1999 | Dahmen et al. | 504/130 |
| 6,221,810 B1 | * | 4/2001 | Kruger et al. | 504/282 |
| 6,410,480 B1 | * | 6/2002 | Muhlebach et al. | 504/105 |
| 6,555,499 B1 | | 4/2003 | Glock et al. | |
| 6,894,005 B1 | | 5/2005 | Maetzke et al. | |
| 6,962,894 B1 | | 11/2005 | Glock | |
| 2005/0164883 A1 | | 7/2005 | Maetzke et al. | |
| 2005/0164886 A1 | | 7/2005 | Glock | |
| 2005/0187110 A1 | | 8/2005 | Maetzke et al. | |

FOREIGN PATENT DOCUMENTS

| | | |
|---|---|---|
| DE | 3939503 A1 | 6/1991 |
| DE | 4331448 A1 | 3/1995 |
| DE | 197 28 568 | 1/1998 |
| EP | 0 508 126 | 10/1992 |
| WO | 9611574 A1 | 4/1996 |
| WO | WO 96 21652 | 7/1996 |
| WO | 9625395 A1 | 8/1996 |
| WO | 9813361 A1 | 4/1998 |
| WO | 9916744 A1 | 4/1999 |
| WO | WO 99 47525 | 9/1999 |
| WO | 0030447 A1 | 6/2000 |
| WO | 0047585 A1 | 8/2000 |
| WO | 0078712 A1 | 12/2000 |
| WO | 03067984 A1 | 8/2003 |

* cited by examiner

Primary Examiner — Sabiha Qazi
(74) Attorney, Agent, or Firm — James Cueva

(57) ABSTRACT

A selective herbicidal composition for controlling grasses and weeds in crops of cultivated plants, comprising
a) a herbicidally effective amount of a compound of formula I

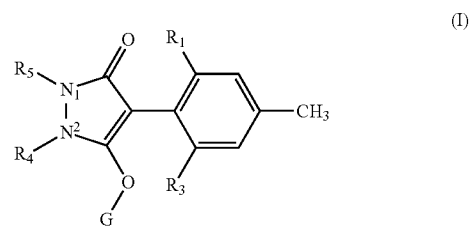

wherein the substituents are defined as given in claim 1;
b) a herbicidally synergistic amount of at least one herbicide selected from the classes of phenoxy-phenoxypropionic acids, hydroxylamines, sulfonylureas, imidazolinones, pyrimidines, triazines, ureas, PPO, chloroacetanilides, phenoxyacetic acids, triazinones, dinitroanilines, azinones, carbamates, oxyacetamides, thiolcarbamates, azole-ureas, benzoic acids, anilides, nitriles, triones and sulfonamides, as well as from the herbicides amitrol, benfuresate, bentazone, cinmethylin, clomazone, chlopyralid, difenzoquat, dithiopyr, ethofumesate, flurochloridone, indanofane, isoxaben, oxaziclomefone, pyridate, pyridafol, quinchlorac, quinmerac, tridiphane and flamprop; and optionally
c) to antagonise the herbicide, an antidotally effective amount of a safener selected from cloquintocet, an alkali, alkaline earth, sulfonium or ammonium cation of cloquintocet, cloquintocet-mexyl, mefenpyr, an alkali, alkaline earth, sulfonium or ammonium cation of mefenpyr and mefenpyr-diethyl; and/or
d) an additive comprising an oil of vegetable or animal origin, a mineral oil, the alkylesters thereof or mixtures of these oils and oil derivatives.

17 Claims, No Drawings

HERBICIDAL COMPOSITION

The present invention relates to novel selective herbicidal synergistic compositions for controlling grasses and weeds in crops of cultivated plants, especially in crops of maize and cereals, which comprise a 3-hydroxy-4-(4-methylphenyl)-5-oxo-pyrazoline herbicides, a synergistically active amount of at least one second herbicide, as well as optionally an oil additive and/or a safener (antidote), and to the use of said compositions for controlling weeds in crops of cultivated plants.

When applying herbicides, the cultivated plants may also suffer severe damage owing to factors that include the concentration of the herbicide and the mode of application, the cultivated plant itself, the nature of the soil, and the climatic conditions such as exposure to light, temperature and rainfall. To counteract this problem and similar ones, the proposal has already been made to use different compounds as safeners which are able to antagonise the harmful action of the herbicide on the cultivated plant, i.e. to protect the cultivated plant while leaving the herbicidal action on the weeds to be controlled virtually unimpaired.

It has, however, been found that the proposed safeners often have a very specific action with respect not only to the cultivated plants but also to the herbicide, and in some cases also subject to the mode of application, i.e. a specific safener will often be suitable only for a specific cultivated plant and a specific class of herbicide or a specific herbicide. For example, it has been found that the safeners cloquintocet or cloquintocet-mexyl and mefenpyr or mefenpyr-diethyl, which are known from EP-A-0 191 736 (comp. 1.316) and WO 91/07874 (example 3) as well as from The Pesticide Manual, 11ed. , British Crop Protection Council, Entry Nos. 154 and 462, can indeed protect the cultivated plants from the phytotoxic action of in particular 3-hydroxy-4-(4-methylphenyl)-5-oxo-pyrazoline derivatives, but partly attenuate the herbicidal action on weeds.

It is known from U.S. Pat. No. 4,834,908 that certain combinations of oil additives can increase the herbicidal action of compounds from the class of cyclohexanediones, benzothiadiazinone dioxides, diphenylether herbicides and aryloxyphenoxy herbicides.

Although the 3-hydroxy-4-(4-methylphenyl)-5-oxo-pyrazoline derivatives are structurally completely different from the compounds disclosed in U.S. Pat. No. 4,834,908, the combination of oil additives of this kind with these 3-hydroxy-4-(4-methylphenyl)-5-oxo-pyrazoline derivatives likewise leads to an increase in herbicidal action, but the cultivated plant is also harmed to a considerable extent. Therefore, this herbicide/oil additive mixture is not suitable for the selective control of weeds in crops of cultivated plants.

It has now surprisingly been found that, when using these special 3-hydroxy-4-(4-methylphenyl)-5-oxo-pyrazoline herbicides, weeds can be selectively controlled with great success without harming the cultivated plant, by applying these compounds in combination with a herbicidally synergistic amount of at least one second herbicide, and optionally also with an additive comprising an oil of vegetable or animal origin or a mineral oil, or the alkylesters thereof or mixtures of these oils and oil derivatives, and/or with the safeners cloquintocet or mefenpyr.

The object of the present invention is thus a selective herbicidal composition comprising, in addition to customary inert formulation assistants such as carriers, solvents and wetting agents, as the active ingredient, a mixture of a) a herbicidally effective amount of a compound of formula I

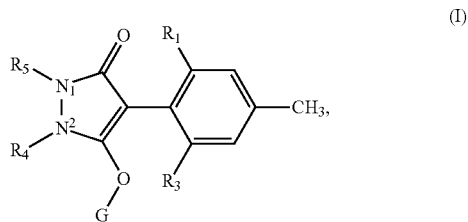

wherein
$R_1$ and $R_3$ independently of one another are halogen, nitro, cyano, $C_1$-$C_4$-alkyl, $C_2$-$C_4$-alkenyl, $C_2$-$C_4$-alkinyl, $C_1$-$C_4$-halogenalkyl, $C_2$-$C_6$-halogenalkenyl, $C_3$-$C_6$-cycloalkyl, halogen-substituted $C_3$-$C_6$-cycloalkyl, $C_2$-$C_6$-alkoxyalkyl, $C_2$-$C_6$-alkylthioalkyl, hydroxy, mercapto, $C_1$-$C_6$-alkoxy, $C_3$-$C_6$-alkenyloxy, $C_3$-$C_6$-alkinyloxy, carbonyl, carboxyl, $C_1$-$C_4$-alkylcarbonyl, $C_1$-$C_4$-hydroxyalkyl, $C_1$-$C_4$-alkoxycarbonyl, $C_1$-$C_4$-alkylthio, $C_1$-$C_4$-alkylsulfinyl, $C_1$-$C_4$-alkylsulfonyl, amino, $C_1$-$C_4$-alkylamino or di-($C_1$-$C_4$-alkyl)-amino; $R_4$ and $R_5$ together signify a group
—C—$R_6$($R_7$)—O—C—$R_8$($R_9$)—C—$R_{10}$($R_{11}$)—C—$R_{12}$($R_{13}$)—($Z_1$),
—C—$R_{14}$($R_{15}$)—C—$R_{16}$($R_{17}$)—O—C—$R_{18}$($R_{19}$)—C—$R_{20}$($R_{21}$)—($Z_2$), or
—C—$R_{22}$($R_{23}$)—C—$R_{24}$($R_{25}$)—C—$R_{26}$($R_{27}$)—O—C—$R_{28}$($R_{29}$)—; ($Z_3$) ;
wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, and $R_{29}$ independently of one another are hydrogen, halogen, $C_1$-$C_4$-alkyl or $C_1$-$C_4$-halogenalkyl, whereby an alkylene ring, which together with the carbon atoms of groups $Z_1$, $Z_2$ or $Z_3$ contains 2 to 6 carbon atoms and may be interrupted by oxygen, may be either anellated or spiro-linked to the carbon atoms of groups $Z_1$, $Z_2$ or $Z_3$, or this alkylene ring overbridges at least one ring atom of groups Gruppen $Z_1$, $Z_2$ or $Z_3$; G is hydrogen, —C($X_1$)—$R_{30}$, —C($X_2$)—$X_3$—$R_{31}$, —C($X_4$)—N($R_{32}$)—$R_{33}$, —SO$_2$—$R_{34}$, an alkaline, alkaline earth, sulfonium or ammonium cation or —P($X_5$)($R_{35}$)—$R_{36}$ or —CH$_2$—$X_6$—$R_{37}$; $X_1$, $X_2$, $X_3$, $X_4$, $X_5$ and $X_5$ independently of one another, are oxygen or sulfur; $R_{30}$, $R_{31}$, $R_{32}$ and $R_{33}$ independently of one another, are hydrogen, $C_1$-$C_{10}$-alkyl, $C_1$-$C_{10}$-halogenalkyl, $C_1$-$C_{10}$-cyanoalkyl, $C_1$-$C_{10}$-nitroalkyl, $C_1$-$C_{10}$-aminoalkyl, $C_1$-$C_5$-alkylamino-$C_1$-$C_5$-alkyl, $C_2$-$C_8$-dialkylamino- $C_1$-$C_5$-alkyl, $C_3$-$C_7$-cyclalkyl-$C_1$-$C_5$-alkyl, $C_2$-$C_{10}$-alkoxy-alkyl, $C_4$-$C_{10}$-alkenyloxy-alkyl, $C_4$-$C_{10}$-alkinyloxy-alkyl, $C_2$-$C_{10}$-alkylthio-alkyl, $C_1$-$C_5$-alkysulfoxyl-$C_1$-$C_5$-alkyl, $C_1$-$C_5$-alkylsulfonyl-$C_1$-$C_5$-alkyl, $C_2$-$C_8$-alkylideneamino-oxy-$C_1$-$C_5$-alkyl, $C_1$-$C_5$-alkylcarbonyl-$C_1$-$C_5$-alkyl, $C_1$-$C_5$-alkoxycarbonyl-$C_1$-$C_5$-alkyl, $C_1$-$C_5$-amino-carbonyl-$C_1$-$C_5$-alkyl, $C_2$-$C_8$-dialkylamino-carbonyl-$C_1$-$C_5$-alkyl, $C_1$-$C_5$-alkylcarbonylamino-$C_1$-$C_5$-alkyl, $C_2$-$C_5$-alkylcarbonyl-($C_1$-$C_5$-alkyl)-aminoalkyl, $C_3$-$C_6$-trialkylsilyl-$C_1$-$C_5$-alkyl, phenyl-$C_1$-$C_5$-alkyl, heteroaryl-$C_1$-$C_5$-alkyl, phenoxy-$C_1$-$C_5$-alkyl, heteroaryloxy-$C_1$-$C_5$-alkyl, $C_2$-$C_5$-alkenyl, $C_2$-$C_5$-halogenalkenyl, $C_3$-$C_8$-cycloalkyl, phenyl; or phenyl substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; or heteroaryl or heteroarylamino; heteroarylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; diheteroarylamino, diheteroarylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; phenylamino, phenylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; diphenylamino, diphenylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $C_3$-$C_7$-cycloalkylamino, $C_3$-$C_7$-cycloalkylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; di-$C_3$-$C_7$-cycloalkylamino, di-$C_3$-$C_7$-cycloalkylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $C_3$-$C_7$-cycloalkoxy or $C_3$-$C_7$-cycloalkoxy substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $R_{34}$, $R_{35}$ and $R_{36}$ independently of one another, are hydrogen, $C_1$-$C_{10}$-alkyl, $C_1$-$C_{10}$-halogenalkyl, $C_1$-$C_{10}$-cyanoalkyl, $C_1$-$C_{10}$-nitroalkyl, $C_1$-$C_{10}$-aminoalkyl, $C_1$-$C_5$-alkylamino-$C_1$-$C_5$-alkyl, $C_2$-$C_8$-dialkylamino- $C_1$-$C_5$-alkyl, $C_3$-$C_7$-cyclalkyl-$C_1$-$C_5$-alkyl, $C_2$-$C_{10}$-alkoxy-alkyl, $C_4$-$C_{10}$-alkenyloxy-alkyl, $C_4$-$C_{10}$-alkinyloxy-alkyl, $C_2$-$C_{10}$-alkylthio-alkyl, $C_1$-$C_5$-alkysulfoxyl-$C_1$-$C_5$-alkyl, $C_1$-$C_5$-alkylsulfonyl-$C_1$-$C_5$-alkyl, $C_2$-$C_8$-alkylideneamino-oxy-$C_1$-$C_5$-alkyl, $C_1$-$C_5$-alkylcarbonyl-$C_1$-$C_5$-alkyl, $C_1$-$C_5$-alkoxycarbonyl-$C_1$-$C_5$-alkyl, $C_1$-$C_5$-amino-carbonyl-$C_1$-$C_5$-alkyl, $C_2$-$C_8$-dialkylamino-carbonyl-$C_1$-$C_5$-alkyl, $C_1$-$C_5$-alkylcarbonylamino-$C_1$-$C_5$-alkyl, $C_2$-$C_5$-alkylcarbonyl-($C_1$-$C_5$-alkyl)-aminoalkyl, $C_3$-$C_6$-trialkylsilyl-$C_1$-$C_5$-alkyl, phenyl-$C_1$-$C_5$-alkyl, heteroaryl-$C_1$-$C_5$-alkyl, phenoxy-$C_1$-$C_5$-alkyl, heteroaryloxy-$C_1$-$C_5$-alkyl, $C_2$-$C_5$-alkenyl, $C_2$-$C_5$-halogenalkenyl, $C_3$-$C_8$-cycloalkyl, phenyl; or phenyl substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; or heteroaryl or heteroarylamino; heteroarylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; diheteroarylamino, diheteroarylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; phenylamino, phenylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; diphenylamino, diphenylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $C_3$-$C_7$-cycloalkylamino, $C_3$-$C_7$-cycloalkylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; di-$C_3$-$C_7$-cycloalkylamino, di-$C_3$-$C_7$-cycloalkylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $C_3$-$C_7$-cycloalkoxy or $C_3$-$C_7$-cycloalkoxy substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $C_1$-$C_{10}$-alkoxy, $C_1$-$C_{10}$-halogenalkoxy, $C_1$-$C_5$-alkylamino, $C_2$-$C_8$-dialkylamino as well as benzyloxy or phenoxy, whereby the benzyl and phenyl groups in turn may be substituted by $C_1$-$C_3$-alkyl, $C_1$-$C_3$-halogenalkyl, $C_1$-$C_3$-alkoxy, $C_1$-$C_3$-halogenalkoxy, halogen, cyano, formyl, acetyl, propionyl, carboxyl, $C_1$-$C_5$-alkoxycarbonyl, methylthio, ethylthio, or nitro; and $R_{37}$ is $C_1$-$C_{10}$-alkyl, $C_1$-$C_{10}$-halogenalkyl, $C_1$-$C_{10}$-cyanoalkyl, $C_1$-$C_{10}$-nitroalkyl, $C_1$-$C_{10}$-aminoalkyl, $C_1$-$C_5$-alkylamino-$C_1$-$C_5$-alkyl, $C_2$-$C_8$-dialkylamino-$C_1$-$C_5$-alkyl, $C_3$-$C_7$-cyclalkyl-$C_1$-$C_5$-alkyl, $C_2$-$C_{10}$-alkoxy-alkyl, $C_4$-$C_{10}$-alkenyloxy-alkyl, $C_4$-$C_{10}$-alkinyloxy-alkyl, $C_2$-$C_{10}$-alkylthio-alkyl, $C_1$-$C_5$-alkysulfoxyl-$C_1$-$C_5$-alkyl, $C_1$-$C_5$-alkylsulfonyl-$C_1$-$C_5$-alkyl, $C_2$-$C_8$-alkylideneamino-oxy-$C_1$-$C_5$-alkyl, $C_1$-$C_5$-alkoxycarbonyl-$C_1$-$C_5$-alkyl, $C_1$-$C_5$-amino-carbonyl-$C_1$-$C_5$-alkyl, $C_2$-$C_8$-dialkylamino-carbonyl-$C_1$-$C_5$-alkyl, $C_1$-$C_5$-alkylcarbonylamino-$C_1$-$C_5$-alkyl, $C_2$-$C_5$-alkylcarbonyl-($C_1$-$C_5$-alkyl)-aminoalkyl, $C_3$-$C_6$-trialkylsilyl-$C_1$-$C_5$-alkyl, phenyl-$C_1$-$C_5$-alkyl, heteroaryl-$C_1$-$C_5$-alkyl, phenoxy-$C_1$-$C_5$-alkyl, heteroaryloxy-$C_1$-$C_5$-alkyl, $C_2$-$C_5$-alkenyl, $C_2$-$C_5$-halogenalkenyl, $C_3$-$C_8$-cycloalkyl, phenyl; or phenyl substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; or heteroaryl or heteroarylamino; heteroarylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; diheteroarylamino, diheteroarylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; phenylamino, phenylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; diphenylamino, diphenylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $C_3$-$C_7$-cycloalkylamino, $C_3$-$C_7$-cycloalkylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; di-$C_3$-$C_7$-cycloalkylamino, di-$C_3$-$C_7$-cycloalkylamino substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; $C_3$-$C_7$-cycloalkoxy or $C_3$-$C_7$-cycloalkoxy substituted by $C_1$-$C_3$-alkyl, $C_1$-$C_3$-halogenalkyl, $C_1$-$C_3$-alkoxy, $C_1$-$C_3$-halogenalkoxy, halogen, cyano or nitro; or $C_1$-$C_{10}$-alkylcarbonyl; as well as salts and diastereoisomers of the compounds of formula I, with the proviso that $R_1$ and $R_3$ are not simultaneously methyl; and;

b) a herbicidally synergistic amount of at least one herbicide selected from the classes of phenoxy-phenoxypropionic acids, hydroxylamines, sulfonylureas, imidazolinones, pyrimidines, triazines, ureas, PPO, chloroacetanilides, phenoxyacetic acids, triazinones, dinitroanilines, azinones, carbamates, oxyacetamides, thiolcarbamates, azole-ureas, benzoic acids, anilides, nitriles, triones and sulfonamides, as well as from the herbicides amitrol, benfuresate, bentazone, cinmethylin, clomazone, chlopyralid, difenzoquat, dithiopyr, ethofumesate, flurochloridone, indanofane, isoxaben, oxaziclomefone, pyridate, pyridafol, quinchlorac, quinmerac, tridiphane and flamprop; and optionally c) to antagonise the herbicide, an antidotally effective amount of a safener selected from cloquintocet, an alkali, alkaline earth, sulfonium or ammonium cation of cloquintocet, cloquintocet-mexyl, mefenpyr, an alkali, alkaline earth, sulfonium or ammonium cation of mefenpyr and mefenpyr-diethyl; and/or d) an additive comprising an oil of vegetable or animal origin, a mineral oil, the alkylesters thereof or mixtures of these oils and oil derivatives.

In the above definitions, halogen is understood to mean fluorine, chlorine, bromine and iodine, preferably fluorine, chlorine and bromine. The alkyl groups occurring in the definitions of the substituents may be for example methyl, ethyl, n-propyl, isopropyl, n-butyl, sec-butyl, isobutyl or tert-butyl, as well as the pentyl and hexyl isomers. Appropriate cycloalkyl substituents contain 3 to 6 carbon atoms and are, for example, cyclopropyl, cyclobutyl, cyclopentyl or cyclohexyl. They may be mono- or polysubstituted by halogen, preferably fluorine, chlorine or bromine. Alkenyl is understood to be for example vinyl, allyl, methallyl, 1-methylvinyl or but-2-en-1-yl Alkinyl signifies for example ethinyl, propargyl, but-2-in-1-yl, 2-methylbutin-2-yl or but-3-in-2-yl. Halogenalkyl groups preferably have a chain length of 1 to 4 carbon atoms. Halogenalkyl is for example fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1.1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Halogenalkenyl may be alkenyl groups that are mono- or polysubstituted by halogen, halogen signifying fluorine, chlorine, bromine and iodine, especially fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluoro-but-2-en-1-yl. Of the $C_2$-$C_6$-alkenyl groups mono-, di- or trisubstituted by halogen, preference is given to those having a chain length of 3 to 5 carbon atoms. Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy, preferably methoxy and ethoxy. Alkoxycarbonyl is preferably acetyl or propionyl. Alkoxycarbonyl signifies for example methoxycarbonyl, ethoxycarbonyl, propoxycarbonyl, iso-propoxycarbonyl, n-butoxycarbonyl, iso-butoxycarbonyl, sec.-butoxycarbonyl or tert.-butoxycarbonyl; preferably methoxycarbonyl or ethoxycarbonyl. Alkylthio groups preferably have a chain length of 1 to 4 carbon atoms. Alkylthio is for example methylthio, ethylthio, propylthio, isopropylthio, n-butylthio, iso-butylthio, sec.-butylthio or tert.-butylthio, preferably methylthio and ethylthio. Alkylsulfinyl is for example methylsulfinyl, ethylsulfinyl, propylsulfinyl, iso-propylsulfinyl, n-butylsulfinyl, iso-butylsulfinyl, sec.-butylsulfinyl, tert.-butylsulfinyl; preferably methylsulfinyl and ethylsulfinyl. Alkylsulfonyl is for example methylsulfonyl, ethylsulfonyl, propylsulfonyl, iso-propylsulfonyl, n-butylsulfonyl, iso-butylsulfonyl, sec.-butylsulfonyl or tert.-butylsulfonyl; preferably methylsulfonyl or ethylsulfonyl. Alkylamino is for example methylamino, ethylamino, n-propylamino, isopropylamino or the isomeric butylamines. Dialkylamino is for example dimethylamino, methylethylamino, diethylamino, n-propylmethylamino, dibutylamino and di-isopropylamino. Alkoxyalkyl groups preferably have 2 to 6 carbon atoms. Alkoxyalkyl signifies for example methoxymethyl, methoxyethyl, ethoxymethyl, ethoxyethyl, n-propoxymethyl, n-propoxyethyl, isopropoxymethyl or iso-propoxyethyl. Alkylthioalkyl signifies for example methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. Phenyl may be present in substituted form. In this case, the substituents may be in ortho-, meta- and/or para-position. Preferred substituent positions are the ortho- and para-positions to the ring connection point. Heteroaryl groups are usually aromatic heterocycles, which contain preferably 1 to 3 hetero atoms selected from nitrogen, oxygen and sulfur. Examples of suitable heterocycles and heteroaromatics are: pyrrolidine, piperidine, pyran, dioxane, azetidine, oxetane, pyridine, pyrimidine, triazine, thiazole, thiadiazole, imidazole oxazole, isoxazole as well as pyrazine, furan, morpholine, piperazine, pyrazole, benzoxazole, benzothiazole, quinoxaline and quinoline. These heterocycles and heteroaromatics may be further substituted, for example by halogen, alkyl, alkoxy, haloalkyl, haloalkoxy, nitro, cyano, thialkyl, alkylamino or phenyl. The $C_2$-$C_{10}$-alkenyl- and alkinylgruppen $R_{34}$ may be mono- or polyunsaturated. They preferably contain 2 to 12, especially 2 to 6 carbon atoms. Alkali, alkaline earth or ammonium cations for the substituents G are for example the cations of sodium, potassium, magnesium, calcium and ammonium. Preferred sulfonium cations are especially trialkylsulfonium cations, in which the alkyl radicals preferably each contain 1 to 4 carbon atoms.

The left free valency of groups $Z_1$, $Z_2$ and $Z_3$ is bonded at position 1 and the right free valency is bonded at position 2 of the pyrazoline ring.

Compounds of formula I, in which an alkylene ring may be anellated or spiro-linked to groups $Z_1$, $Z_2$ and $Z_3$, giving 2 to 6 carbon atoms together with the carbon atoms of groups $Z_1$, $Z_2$ and $Z_3$, have for example the following structure:

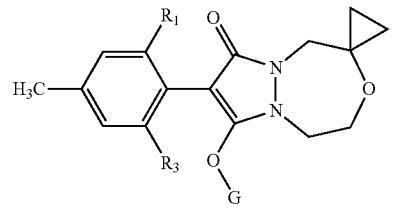

(spiro-linked) or

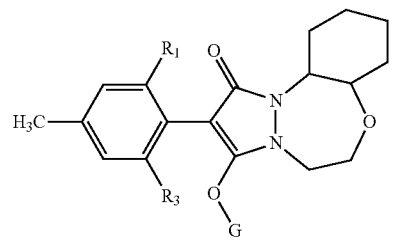

(anellated).

Compounds of formula I, in which an alkylene ring in groups $Z_1$, $Z_2$ or $Z_3$ overbridges at least one ring atom of groups $Z_1$, $Z_2$ or $Z_3$, have for example the following structure:

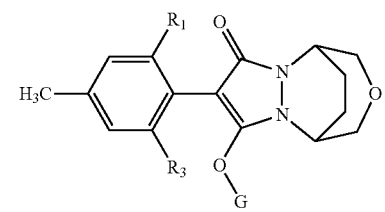

(overbridged).

Preferred herbicides of formula I for the composition according to the invention are characterised in that $R_1$ and $R_3$, independently of one another, signify ethyl, halogenethyl, ethinyl, $C_1$-$C_2$-alkoxy or $C_1$-$C_2$-halogenalkoxy.

Also preferred are those compositions according to the invention in which $R_4$ and $R_5$ together form a group $Z_2$—C—$R_{14}(R_{15})$—C—$R_{16}(R_{17})$—O—C—$R_{18}(R_{19})$—C—$R_{20}(R_{21})$—($Z_2$), wherein $R_{14}$, $R_{15}$, $R_{16}$, $R_{17}$, $R_{18}$, $R_{19}$, $R_{20}$ and $R_{21}$ most preferably signify hydrogen.

A further preferred group of compositions according to the invention is characterised in that $R_{30}$, $R_{31}$, $R_{32}$ and $R_{33}$ independently of each other, signify hydrogen, $C_1$-$C_8$-alkyl, $C_1$-$C_8$-halogenalkyl, $C_1$-$C_8$-cyanoalkyl, $C_1$-$C_8$-nitroalkyl, $C_1$-$C_8$-aminoalkyl, $C_2$-$C_5$-alkenyl, $C_2$-$C_5$-halogenalkenyl, $C_3$-$C_8$-cycloalkyl, $C_1$-$C_8$-alkylamino-$C_1$-$C_5$-alkyl, $C_2$-$C_8$-dialkylamino-$C_2$-$C_5$-alkyl, $C_3$-$C_7$-cycloalkyl-$C_1$-$C_5$-alkyl, $C_2$-$C_4$-alkoxy-alkyl, $C_4$-$C_6$-alkenyloxy-alkyl, $C_4$-$C_6$-alkinyloxy-alkyl, $C_2$-$C_4$-alkylthio-alkyl, $C_1$-$C_4$-alkysulfinyl-$C_1$-$C_2$-alkyl, $C_1$-$C_2$-alkylsulfonyl-$C_1$-$C_2$-alkyl, $C_2$-$C_4$-alkylideneamino-oxy-$C_1$-$C_2$-alkyl, $C_1$-$C_5$-alkylcarbonyl-$C_1$-$C_2$-alkyl, $C_1$-$C_5$-alkoxycarbonyl-$C_1$-$C_2$-alkyl, $C_1$-$C_5$-aminocarbonyl-$C_1$-$C_2$-alkyl, $C_2$-$C_8$-dialkylamino-carbonyl-$C_1$-$C_2$-alkyl, $C_1$-$C_5$-alkylcarbonylamino-$C_1$-$C_2$-alkyl, $C_2$-$C_5$-alkylcarbonyl-($C_1$-$C_2$-alkyl)-aminoalkyl, $C_3$-$C_6$-trialkylsilyl-$C_1$-$C_5$-alkyl, phenyl-$C_1$-$C_2$-alkyl, heteroaryl-$C_1$-$C_2$-alkyl, phenoxy-$C_1$-$C_2$-alkyl, heteroaryloxy-$C_1$-$C_2$-alkyl, phenyl or heteroaryl; $R_{34}$, $R_{35}$ and $R_{36}$ independently of each other, signify hydrogen, $C_1$-$C_8$-alkyl, $C_1$-$C_8$-halogenalkyl, $C_1$-$C_8$-cyanoalkyl, $C_1$-$C_8$nitroalkyl, $C_1$-$C_8$-aminoalkyl, $C_2$-$C_5$-alkenyl, $C_2$-$C_5$-halogenalkenyl, $C_3$-$C_8$-cycloalkyl, $C_1$-$C_5$-alkylamino-$C_1$-$C_5$-alkyl, $C_2$-$C_8$-dialkylamino-$C_1$-$C_5$-alkyl, $C_3$-$C_7$-cycloalkyl-$C_1$-$C_5$-alkyl, $C_2$-$C_4$-alkoxy-alkyl, $C_4$-$C_6$-alkenyloxy-alkyl, $C_4$-$C_6$-alkinyloxy-alkyl, $C_2$-$C_4$-alkylthio-alkyl, $C_1$-$C_4$-alkysulfinyl-$C_1$-$C_2$-alkyl, $C_1$-$C_2$-alkylsulfonyl-$C_1$-$C_2$-alkyl, $C_2$-$C_4$-alkylideneamino-oxy-$C_1$-$C_2$-alkyl, $C_1$-$C_5$-alkylcarbonyl-$C_1$-$C_2$-alkyl, $C_1$-$C_5$-alkoxycarbonyl-$C_1$-$C_2$-alkyl, $C_1$-$C_5$-aminocarbonyl-$C_1$-$C_2$-alkyl, $C_2$-$C_8$-dialkylamino-carbonyl-$C_1$-$C_2$-alkyl, $C_1$-$C_5$-alkylcarbonylamino-$C_1$-$C_2$-alkyl, $C_2$-$C_5$-alkylcarbonyl-($C_1$-$C_2$-alkyl)-aminoalkyl, $C_3$-$C_6$-trialkylsilyl-$C_1$-$C_5$-alkyl, phenyl-$C_1$-$C_2$-alkyl, heteroaryl-$C_1$-$C_2$-alkyl, phenoxy-$C_1$-$C_2$-alkyl, heteroaryloxy-$C_1$-$C_2$-alkyl, phenyl or heteroaryl, benzyloxy or phenoxy, whereby the benzyl and phenyl groups in turn may be substituted by halogen, nitro, cyano, amino, dimethylamino, hydroxy, methoxy, ethoxy, methylthio, ethylthio, formyl, acetyl, propionyl, carboxyl, $C_1$-$C_5$-alkoxycarbonyl or $C_1$- or $C_2$-halogenalkyl; and $R_{37}$ signifies $C_1$-$C_8$-alkyl, $C_1$-$C_6$halogenalkyl, $C_1$-$C_8$-cyanoalkyl, $C_1$-$C_8$-nitroalkyl, $C_1$-$C_8$-aminoalkyl, $C_2$-$C_5$-alkenyl, $C_2$-$C_5$-halogenalkenyl, $C_3$-$C_8$-cycloalkyl, $C_1$-$C_5$-alkylamino-$C_1$-$C_5$-alkyl, $C_2$-$C_8$-dialkylamino-$C_1$-$C_5$-alkyl, $C_3$-$C_7$-cycloalkyl-$C_1$-$C_5$-alkyl, $C_2$-$C_4$-alkoxy-alkyl, $C_4$-$C_6$-alkenyloxy-alkyl, $C_4$-$C_6$-alkinyloxy-alkyl, $C_2$-$C_4$-alkylthio-alkyl, $C_1$-$C_4$-alkysulfinyl-$C_1$-$C_2$-alkyl, $C_1$-$C_2$-alkylsulfonyl-$C_1$-$C_2$-alkyl, $C_2$-$C_4$-alkylideneamino-oxy-$C_1$-$C_2$-alkyl, $C_1$-$C_5$-alkylcarbonyl-$C_1$-$C_2$-alkyl, $C_1$-$C_5$-alkoxycarbonyl-$C_1$-$C_2$-alkyl, $C_1$-$C_5$-amino-carbonyl-$C_1$-$C_2$-alkyl, $C_2$-$C_8$-dialkylamino-carbonyl-$C_1$-$C_2$-alkyl, $C_1$-$C_5$-alkylcarbonylamino-$C_1$-$C_2$-alkyl, $C_2$-$C_5$-alkylcarbonyl-($C_1$-$C_2$-alkyl)-aminoalkyl, $C_3$-$C_6$-trialkylsilyl-$C_1$-$C_5$-alkyl, phenyl-$C_1$-$C_2$-alkyl, heteroaryl-$C_1$-$C_2$-alkyl, phenoxy-$C_1$-$C_2$-alkyl, heteroaryloxy-$C_1$-$C_2$-alkyl, phenyl or heteroaryl, benzyloxy or phenoxy, whereby the benzyl and phenyl groups in turn may be substituted by halogen, nitro, cyano, amino, dimethylamino, hydroxy, methoxy, ethoxy, methylthio, ethylthio, formyl, acetyl, propionyl, carboxyl, $C_1$-$C_2$-alkoxycarbonyl or $C_1$- or $C_2$-halogenalkyl; or $R_{37}$ signifies $C_1$-$C_8$alkylcarbonyl.

Especially preferred are those compositions according to the invention in which, in formula I, $R_{30}$, $R_{31}$, $R_{32}$ and $R_{33}$, independently of each other, signify hydrogen, $C_1$-$C_8$-alkyl, $C_1$-$C_8$-halogenalkyl, $C_2$-$C_5$-alkenyl, $C_2$-$C_5$-halogenalkenyl, $C_3$-$C_8$-cycloalkyl, $C_3$-$C_7$-cycloalkyl-$C_1$-$C_2$-alkyl, $C_2$-$C_4$-alkoxy-alkyl, phenyl, heteroaryl, phenyl-$C_1$-$C_2$-alkyl, heteroaryl-$C_1$-$C_2$-alkyl, phenoxy-$C_1$-$C_2$-alkyl, heteroaryloxy-$C_1$-$C_2$-alkyl; $R_{34}$, $R_{35}$ and $R_{36}$ independently of each other, signify hydrogen, $C_1$-$C_8$-alkyl, $C_1$-$C_8$-halogenalkyl, $C_2$-$C_5$-alkenyl, $C_2$-$C_5$-halogenalkenyl, $C_3$-$C_8$-cycloalkyl, $C_3$-$C_7$-cycloalkyl-$C_1$-$C_2$-alkyl, $C_2$-$C_4$-alkoxy-alkyl, phenyl, heteroaryl, phenyl-$C_1$-$C_2$-alkyl, heteroaryl-$C_1$-$C_2$-alkyl, phenoxy-$C_1$-$C_2$-alkyl, heteroaryloxy-$C_1$-$C_2$-alkyl, $C_1$-$C_6$-alkoxy, $C_1$-$C_3$-alkylamino or di-($C_1$-$C_3$-alkyl)-amino; and $R_{37}$ signifies $C_1$-$C_8$-alkyl, $C_1$-$C_8$-halogenalkyl, $C_2$-$C_5$-alkenyl, $C_2$-$C_5$-halogenalkenyl, $C_3$-$C_8$-cycloalkyl, $C_3$-$C_7$-cycloalkyl-$C_1$-$C_2$-alkyl, $C_2$-$C_4$-alkoxy-alkyl, phenyl, heteroaryl, phenyl-$C_1$-$C_2$-alkyl, heteroaryl-$C_1$-$C_2$-alkyl, phenoxy-$C_1$-$C_2$-alkyl, heteroaryloxy-$C_1$-$C_2$-alkyl, $C_1$-$C_6$-alkoxy, $C_1$-$C_3$-alkylamino, di-($C_1$-$C_3$-alkyl)-amino or $C_1$-$C_8$-alkylcarbonyl.

Of the compositions according to the invention, particular preference is also given to those which contain as the herbicidally effective component a mixture of a compound of formula I and a synergistically effective amount of at least one herbicide selected from diclofop-methyl, fluazifop-P-butyl-quizalafop-P-ethyl, propaquizafop, clodinafop-P-propargyl, cyhalfop-butyl, fenoxaprop-P-ethyl, haloxyfop-methyl, haloxyfop-etoethyl, sethoxidim, alloxydim, clethodim, clefoxydim, cycloxydim, tepralkoxydim, tralkoxydim butroxidim, amidosulfuron, azimsulfuron, bensulfuron-methyl, chlorimuron-ethyl, cinosulfuron, chlorsulfuron, chlorimuron, cyclosulfamuron, ethametsulfuron-methyl, ethoxysulfuron, fluazasulfuron, flupyrsulfuron, imazosulfuron, iodosulfuron (CAS RN 144550-36-7 and 185119-76-0), metsulfuron-methyl, nicosulfuron, oxasulfuron, primisulfuron, pyrazosulfuron-ethyl, sulfosulfuron, rimsulfuron, thifensulfuron-methyl, triasulfuron, tribenuron-methyl, triflusulfuron-methyl, prosulfuron, flucarbazon, tritosulfuron CAS RN 142469-14-5, imazethapyr, imazamethabenz, imazamethapyr, imazaquin, imazamox, imazapyr, pyrithiobac-sodium, pyriminobac, bispyribac-sodium, atrazin, butracil, simazin, simethryne, terbutryne, terbuthylazine, trimexyflam, isoproturon, chlortoluron, diuron, dymron, fluometuron, linuron, methabenzthiazuron, glyphosate, sulfosate, glufosinate, nitrofen, bifenox, acifluorfen, lactofen, oxyfluorfen, ethoxyfen, fluoroglycofen, fomesafen, halosafen, azafenidin (CAS RN.-68049-83-2), benzfendizone (CAS RN 158755-95-4), butafenacil (CAS RN 158755-95-4), carfentrazone-ethyl, cinidon-ethyl (CAS RN 142891-20-1), flumichlorac-pentyl, flumioxazin, fluthiacet-methyl, oxadiargyl (CAS RN 39807-15-3), oxadiazon, pentoxazon (CAS RN 110956-75-7), sulfentrazone, fluazolate (CAS RN 174514-07-9), pyraflufen-ethyl, alachlor, acetochlor, butachlor, dimethachlor, dimethenamid, S-dimethenamid, metazachlor, metolachlor, S-metolachlor, pretilachlor, propachlor, propisochlor, thenylchlor, pethoamid (CAS RN 106700-29-2), 2,4-D, fluroxypyr, MCPA, MCPP, MCPB, trichlorpyr, mecropop-P, hexazinon, metamitron, metribuzin, oryzalin, pendimethalin, trifluralin, chloridazon, norflurazon, chlorpropham, desmedipham, phenmedipham, propham, mefenacet, fluthiacet, butylate, cycloate, diallate, EPTC, esprocarb, molinate, prosulfocarb, thiobencarb, triallate, fentrazamide (CAS RN158237-07-1), cafenstrole, dicamba, picloram, diflufenican, propanil, bromoxynil, dichlobenil, ioxynil, sulcotrione, mesotrione (CAS RN 104206-82-8), isoxaflutole, isoxachlortole (CAS RN 141112-06-3), flucarbazone (CAS RN 181274-17-9), propoxycarbazone (CAS RN 145026-81-9 and 181274-15-7 (sodium salt)), foramsulfuron CAS RN 173159-57-4, penoxsulam (CAS RN 219714-96-2), trifloxysulfuron (CAS RN 145099-21-4 and 199119-58-9 (sodium salt)), pyriftalid (CAS RN 135186-78-6), trifloxysulfuron CAS RN 145099-21-4 and 199119-58-9 (sodium salt)), pyriftalid (CAS RN 135186-78-6), flufenpyr-ethyl (CAS RN 188489-07-8), profluazol (CAS RN 190314-43-3), pyraclonil (CAS RN 158353-15-2), benfluamid (CAS RN 113604-08-7), picolinafen (CAS RN 137641-05-5), amicarbazone (CAS RN 129909-90-6), flufenpyr-ethyl (CAS RN 188489-07-8), profluazol (CAS RN 190314-43-3), pyraclonil (CAS RN 158353-15-2), benfluamid (CAS RN 113604-08-7), picolinafen (CAS RN 137641-05-5), amicarbazone (CAS RN 129909-90-6), chlorasulam, diclosulam (CAS RN 145701-21-9), florasulam, flumetsulam, metosulam, amitrol, benfuresate, bentazone, cinmethylin, clomazone, chlopyralid, difenzoquat, dithiopyr, ethofumesate, flurochloridone, indanofane, isoxaben, oxaziclomefone (CAS RN 153197-14-9), pyridate, pyridafol (CAS RN 40020-01-7), quinchlorac, quinmerac, tridiphane and flamprop. The abbreviation CAS RN indicates the registration number in Chemical Abstracts.

The compositions according to the invention preferably contain
a) a herbicide of formula I in combination with:
b) a herbicidally synergistic amount of a second herbicide according to the invention,
c) a safener and
d) an oil additive.

Of the synergistically active herbicides b), those of the class of sulfonylureas and phenoxy-phenoxypropionic acids are preferred, with particular preference being given for example to clodinafop-propargyl known from The Pesticide Manual, 11$^{th}$ ed., British Crop Protection Council, Entry No. 147 and triasulfurone known from The Pesticide Manual, 11$^{th}$ ed., British Crop Protection Council, Entry No. 723. An especially preferred safener c) is cloquintocetmexyl. In terms of the present invention, MERGE® and Actiprom® are especially notable as suitable oil additives.

If not otherwise stated, the above-mentioned components of the compound of formula I are known from The Pesticide Manual, Eleventh Edition, 1997, BCPC. The components of the compound of formula I may, if desired, also be present in the form of esters or salts, as named e.g. in The Pesticide Manual, Eleventh Edition, 1997, BCPC. Butafenacil is known from U.S. Pat. No. 5,183,492. Pethoamid has the CAS registration number 106700-29-2. Mesotrione is known from U.S. Pat. No. 5,006,158.

The compositions according to the invention may also contain salts which the compounds of formula I can form with acids. Suitable acids for the formation of the acid addition salts are both organic and inorganic acids. Examples of such acids are hydrochloric acid, hydrobromic acid, nitric acid, phosphoric acids, sulfuric acid, acetic acid, propionic acid, butyric acid, valeric acid, oxalic acid, malonic acid, fumaric acid, organic sulfonic acids, lactic acid, tartaric acid, citric acid and salicylic acid. The salts of compounds of formula I with acidic hydrogen are also alkali metal salts, e.g. sodium and potassium salts; alkaline earth metal salts, e.g. calcium and magnesium salts; ammonium salts, i.e. unsubstituted ammonium salts and mono- or polysubstituted ammonium salts, as well as salts with other organic nitrogen bases. Corresponding salt-forming components are alkali and alkaline earth metal hydroxides, especially the hydroxides of lithium, sodium, potassium, magnesium or calcium, with special significance being given to those of sodium or potassium.

Illustrative examples of amines suitable for forming ammonium salts are ammonia, as well as primary, secondary, and tertiary $C_1$-$C_{18}$-alkylamines, $C_1$-$C_4$-hydroxyalkylamines and $C_2$-$C_4$-alkoxyalkylamines, typically methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methyl ethylamine, methyl isopropylamine, methyl hexylamine, methyl nonylamine, methyl pentadecylamine, methyl octadecylamine, ethyl butylamine, ethyl heptylamine, ethyl octylamine, hexyl heptylamine, hexyl octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines such as pyridine, quinoline, isoquinoline, morpholine, N-methylmorpholine, thiomorpholine, piperidine, pyrrolidine, indoline, quinuclidine and azepine; primary arylamines such as anilines, methoxyanilines, ethoxyanilines, o-, m- and p-toluidines, phenylendiamines, benzidines, naphthylamines and o-, m- and p-chloroanilines. Preferred amines are triethylamine, isopropylamine and diisopropylamine.

In the methods described in this application, if non-chiral educts are used, the unsymmetrically substituted compounds of formula I generally occur as racemates. The stereoisomers may then be separated by known methods, such as fractional crystallisation following salt formation with optically pure bases, acids or metal complexes, or by chromatographic methods, e.g. high pressure liquid chromatography (HPLC) on acetyl cellulose, on the basis of physical-chemical properties. In the present invention, the compounds of formula I are understood to include both the concentrated and optically pure forms of each stereoisomer, and the racemates or diastereoisomers. If there is no specific reference to the individual optical antipodes, the racemic mixtures under the given formula are understood to be those which are obtained in the indicated preparation process. If there is an aliphatic C=C-double bond, then geometric isomerism may also occur.

Depending on the type of substituents, the compounds of formula I may also exist as geometric and/or optical isomers and isomer mixtures, and as tautomers and tautomer mixtures. For example, the compounds of formula I, in which the group G signifies hydrogen, may exist in the following tautomeric equilibria.

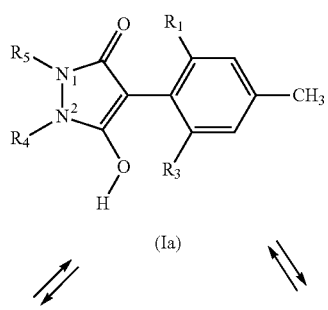

(Ia)

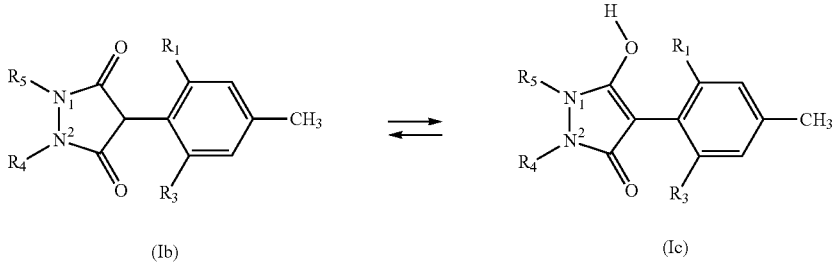

(Ib)    (Ic)

If G is other than hydrogen and Z signifies the group $Z_1$ or $Z_3$, or if G is other than hydrogen and $Z_2$ is unsymmetrically substituted, anellated or spiro-linked, the compound of formula I may exist as the isomer of formula Id

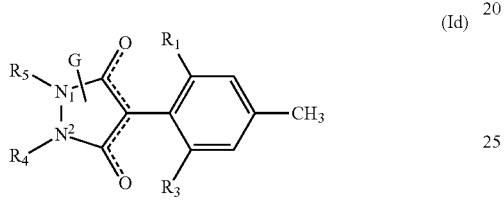

(Id)

Methods of preparing compounds, which are different in respect of the significance of substituents $R_4$ and $R_5$ from the compounds of formula I of the present invention, are described for example in WO 96/21652. The compounds of formula I of the present invention may be prepared in analogous manner to the methods described in WO 96/21652.

The compounds of formula II used as starting products for such methods

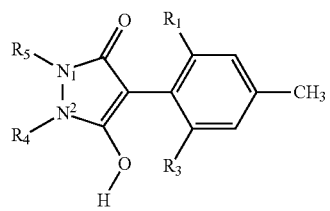

(II)

wherein $R_1$, $R_3$, $R_4$ and $R_5$ are defined as given in formula I, may be prepared for example whereby a compound of formula III

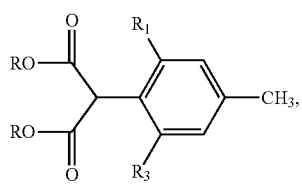

(III)

in which R is $C_1$-$C_6$-alkyl, $C_1$-$C_6$-halogenalkyl, preferably methyl, ethyl or trichloroethyl, and $R_1$ and $R_3$ are defined as given in formula I, is reacted in an inert organic solvent, optionally in the presence of a base, with a compound of formula IV or IVa

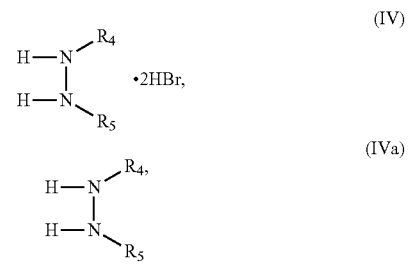

wherein $R_4$ and $R_5$ are defined as in formula I. Further preparation methods for compounds of formula II are also described for example in WO 92/16510.

The compounds of formula III are either known or may be produced analogously to known methods. Methods for the preparation of compounds of formula III, as well as the reaction thereof with hydrazines, are described for example in WO 97/02243. Compounds of formula III, wherein R is $C_1$-$C_6$-alkyl, $C_1$-$C_6$-halogenalkyl, preferably methyl, ethyl or trichloroethyl, and $R_1$, $R_2$ and $R_3$ are defined as given in formula I, may be prepared by methods known to those skilled in the art. For example, compounds of formula III, wherein R is $C_1$-$C_6$-alkyl, $C_1$-$C_6$-halogenalkyl, preferably methyl, ethyl or trichloroethyl, and $R_1$, $R_2$ and $R_3$, independently of each other, are $C_1$-$C_4$-alkyl, $C_2$-$C_4$-alkenyl, $C_2$-$C_4$-alkinyl, may be prepared by the cross-coupling method of Stille (J. K. Stille, Angew. Chem. 1986, 98, 504-519), Sonogashira (K. Sonogashira et al., Tetrahedron Lett. 1975, 4467-4470), Suzuki (N. Miyaura, A. Suzuki, Chem. Rev. 1995, 95, 2457-2483) or Heck (R. F. Heck, Org. React. 1982, 27, 345-390) with optional subsequent hydrogenation. The following reaction scheme illustrates this procedure:

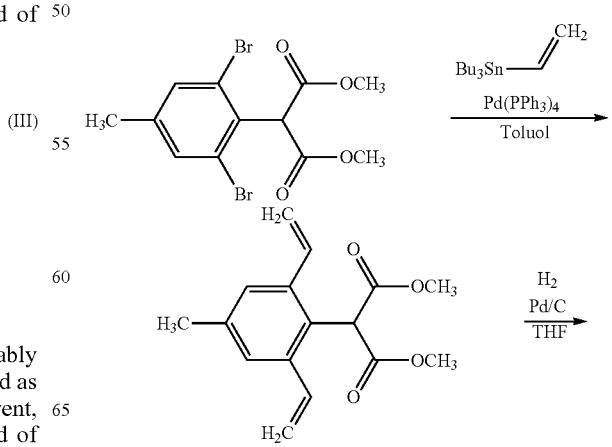

-continued

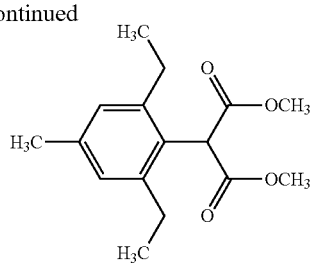

The compounds of formula IV and IVa are either known or may be produced analogously to known methods. Preparation methods for compounds of formula IV are described for example in WO 95/00521. These compounds may be produced e.g. whereby a compound of formula V

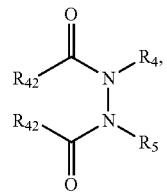

(V)

wherein $R_{42}$ signifies hydrogen, $C_1$-$C_4$-alkyl, $C_1$-$C_6$-alkoxy, $C_1$-$C_6$-halogenalkoxy, benzyloxy, preferably hydrogen, methyl, methoxy, ethoxy, trichloroethoxy, t-butoxy or benzyloxy and $R_4$ and $R_5$ are defined as given in formula I, are heated in an inert solvent in the presence of a base or an acid. Compounds of formula V, wherein $R_{42}$ signifies hydrogen, $C_1$-$C_4$-alkyl, $C_1$-$C_6$-alkoxy, $C_1$-$C_6$-halogenalkoxy, benzyloxy, preferably hydrogen, methyl, methoxy, ethoxy, trichloroethoxy, t-butoxy or benzyloxy and $R_4$ and $R_5$ are defined as given in formula I, may be produced for example whereby a compound of formula VI

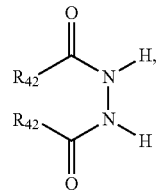

(VI)

wherein $R_{42}$ signifies hydrogen, $C_1$-$C_4$-alkyl, $C_1$-$C_6$-alkoxy, $C_1$-$C_6$-halogenalkoxy, benzyloxy, preferably hydrogen, methyl, methoxy, ethoxy, trichloroethoxy, t-butoxy or benzyloxy, is reacted in the presence of a base and an inert solvent with a compound of formula VII

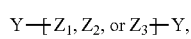

(VII)

wherein Y signifies halogen, alkyl/aryl sulfonates —$OSO_2R_{43}$, preferably bromine, chlorine, iodine, mesylate ($R_{43}$=$CH_3$), triflate ($R_{43}$=$CF_3$) or tosylate ($R_{43}$=p-tolyl) and $Z_1$, $Z_2$ and $Z_3$ are defined as given in formula I. In formula VII, the free valencies of groups $Z_1$, $Z_2$ and $Z_3$ are each bonded to the group Y. Compounds of formulae VI and VII are known or may be prepared analogously to methods known to those skilled in the art.

Compounds of formula IV, wherein $R_4$ and $R_5$ together are a group $Z_2$—C—$R_{14}(R_{15})$—C—$R_{16}(R_{17})$—O—C—$R_{18}$($R_{19}$)—C—$R_{20}(R_{21})$—($Z_2$), wherein $R_{14}$, $R_{15}$, $R_{16}$, $R_{17}$, $R_{18}$, $R_{19}$, $R_{20}$ and $R_{21}$ signify hydrogen, may be produced e.g. in accordance with the following reaction scheme:

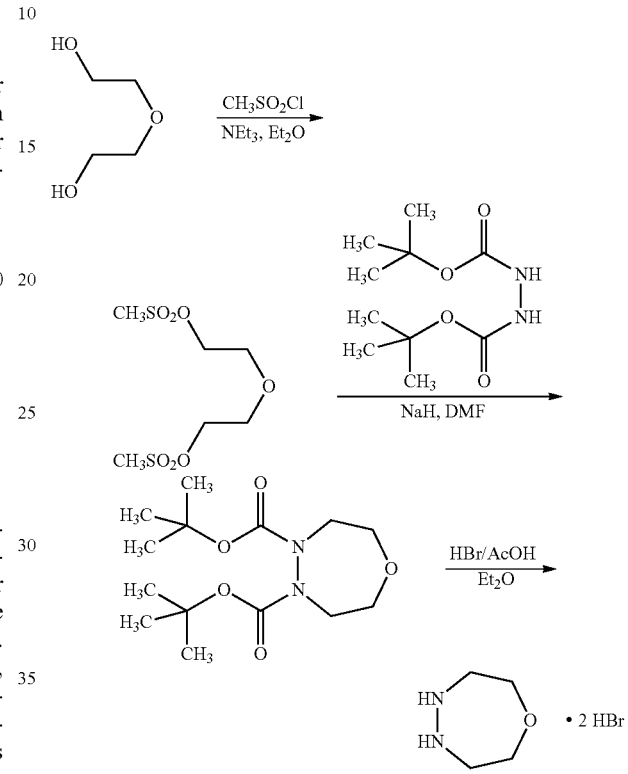

The end products of formula I can be isolated in conventional manner by concentrating the reaction mixture and/or removing the solvent by evaporation and by recrystallising or triturating the solid residue in a solvent in which it is not readily soluble, typically an ether, an alkane, an aromatic hydrocarbon or a chlorinated hydrocarbon or by chromatography. Salts of compounds of formula I may be prepared in a known manner. Preparation methods of this kind are described for example in WO 96/21652.

PREPARATION EXAMPLES

Example P1: Preparation of (1):

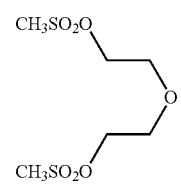

A solution of 177.6 g of methane sulfochloride in 400 ml of diethylether is added dropwise over the course of one hour to a solution, cooled to −10° C., of 80.6 g (0.76 mols) of diethylene glycol and 159.9 g (1.58 mols) of triethylamine in 1500 ml of diethylether, whereby the temperature is maintained at below 5° C. After stirring for 30 minutes at a temperature of 0° C., the cooling means is removed. After 2 hours, 12 ml of triethylamine and 12 ml of methane sulfochloride are added at a temperature of 20° C., and stirring continues for a further 4 hours. The white suspension obtained is subsequently added to a suction filter and the residue washed twice with 300 ml of diethylether. The filtration material is taken up in 2000 ml of ethyl acetate, the suspension stirred for 30 minutes at room temperature and filtration is effected again. The filtrate obtained is concentrated by evaporation and the residue used without further purification for the next reaction. 216.5 g of the desired crude product (1) are obtained in the form of white crystals.

Example P2:

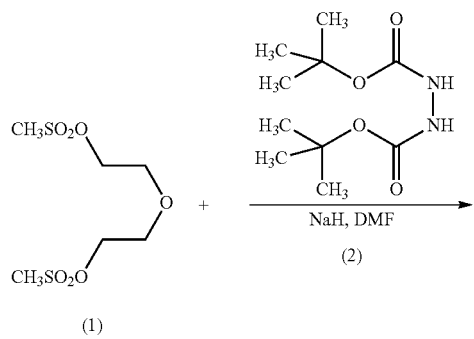

(1)

A solution of 68.78 g (0.30 mols) of (2) in 140 ml of dimethylformamide is added dropwise over the course of 30 minutes to a suspension, cooled to 5° C., of 23.9 g (0.60 mols) of 60% sodium hydride in 500 ml of dimethylformamide. The cooling means is removed and stirring is effected until the reaction mixture has reached a temperature of 20° C. Then, heating is effected for a short time to a temperature of 30 to 40° C. in order to complete the removal of hydrogen. After cooling to a temperature of 0 to 5° C., a solution of 80 g (0.305 mols) of (1) in 160 ml of dimethylformamide is added dropwise over the course of 30 minutes, whereby the temperature is maintained at 0 to 5° C. After removing the cooling means and stirring for 3 hours at room temperature, and also for 45 minutes at ca. 40° C., the reaction mixture is added to a mixture of saturated ammonium chloride solution, ice and tert.-butylmethyl ether, the phases are separated and subsequently the organic phase is washed twice with water. After drying the organic phase with sodium sulphate, concentrating by evaporation and further drying at a temperature of 40° C. under vacuum, 92.2 g of (3) are obtained in the form of a slightly yellow oil. The crude product is used in the next reaction without further purification.

Example P3:

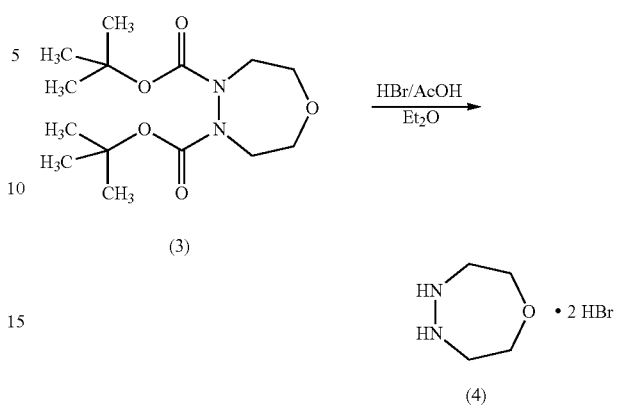

160.5 ml of a 33% solution of hydrogen bromide in glacial acetic acid is added dropwise over the course of 30 minutes to a solution, cooled to 0° C., of 92.2 g (0.305 mols) of (3) in 1200 ml of diethylether. After removing the cooling means and subsequently stirring for 22 hours at 20° C. and for 27 hours under reflux, the white suspension obtained is added to a suction filter, washed with diethylether, and then the residue of filtration is dried over $P_2O_5$ under vacuum at a temperature of 50 to 60° C. The product (4) is obtained in a yield of 52.9 g in the form of a white solid.

Example P4:

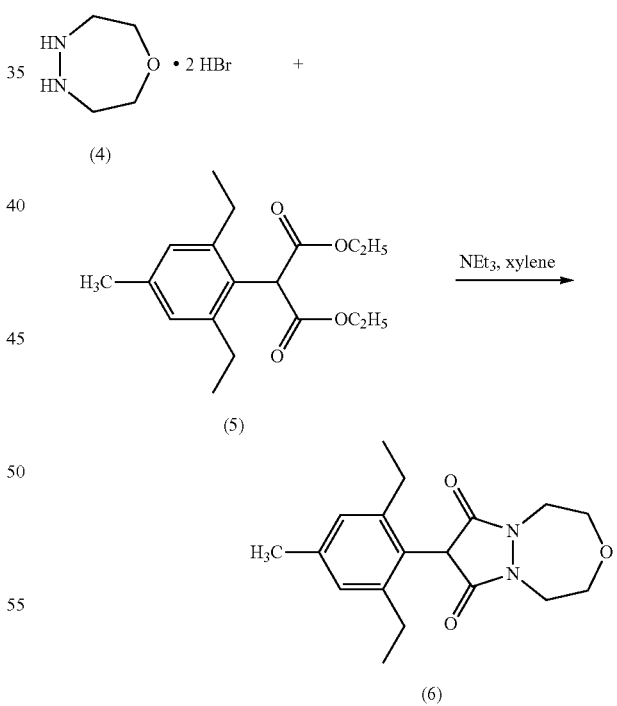

10.61 ml (76 mmols) of triethylamine are added to a suspension of 4.4 g (16.5 mmols) of (4) in 175 ml of xylene, and degassed (4×vacuum/argon). The yellow suspension is subsequently heated to a temperature of 60° C. and stirred for 3 hours. Then, 5.07 g (16.5 mmols) of (5) are added and heating effected to a bath temperature of 140° C., in order to continuously distill off the excess triethylamine and the resulting ethanol. After 3 hours, the reaction mixture is cooled to a temperature of 40° C. and added to 100 ml of an ice/water mixture. The reaction mixture is rendered alkaline with aqueous 1N sodium hydroxide solution and the aqueous phase (contains the product) is washed twice with ethyl acetate. After twice washing back the organic phase with aqueous 1N sodium hydroxide solution, the aqueous phases are combined, the remaining xylene distilled off and the combined aqueous phases adjusted to pH 2-3 with 4N HCl whilst cooling. The precipitating product is added to a suction filter, the residue of filtration washed with water and briefly with hexane, and then the residue of filtration is dried in a vacuum at a temperature of 60° C. over $P_2O_5$. 4.08 g of (6) solid are obtained with a melting point of 189-191° C. (decomp.).

Example P5:

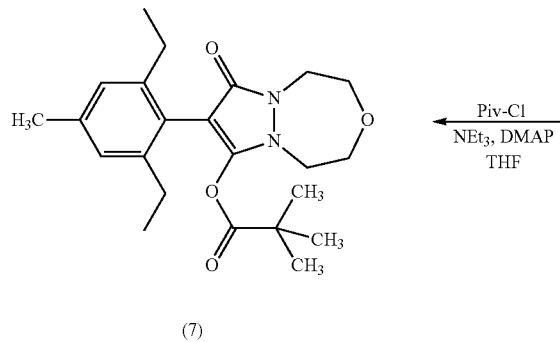

(7)

A catalytic amount of 4-dimethylaminopyridine is added to a solution, cooled to a temperature of 0° C., of 1 g (3.2 mmols) of (6) and 0.65 g (6.4 mmols) of triethylamine in 30 ml of tetrahydrofuran. Then, 0.49 g (4.1 mmols) of pivaloyl chloride are added dropwise. After stirring for 30 minutes at a temperature of 0° C., the cooling means is removed and stirring continues for 60 minutes. Subsequently, the reaction mixture is added to saturated aqueous sodium chloride solution and the organic phase is separated. The organic phase is dried over magnesium sulfate, filtered and concentrated by evaporation. After purification by chromatography and recrystallisation from diethylether, 1.07 g of (7) are obtained with a melting point of 122 to 123° C.

Example P6: Preparation of (8):

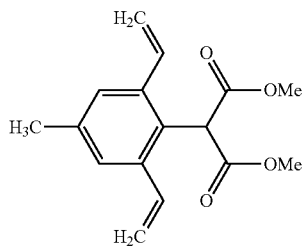

To a solution of 20 g of 2-(2,6-dibromo-4-methylphenyl)-malonic acid dimethylester (known from WO 96/35664) (52.6 mmols) in 400 ml of toluene (3×degassed, vacuum/argon) are added first of all 36.7 g (0.116 mmols) of tributylvinyl stannane and then 2 g of tetrakis-triphenylphosphine-palladium. The reaction mixture is then stirred for 9 hours at a temperature of 90 to 95° C. After filtration through Hyflo and concentrating on a rotary evaporator, the mixture is purified by chromatography to give 15.3 g of (8) in the form of a yellow oil, which is used in the next reaction without further purification.

Example P7:

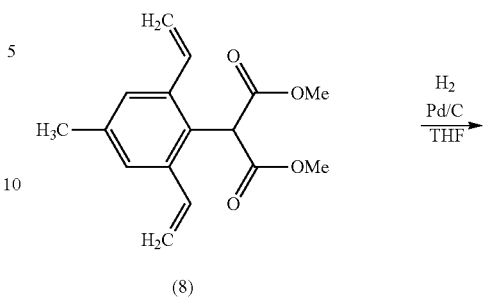

-continued

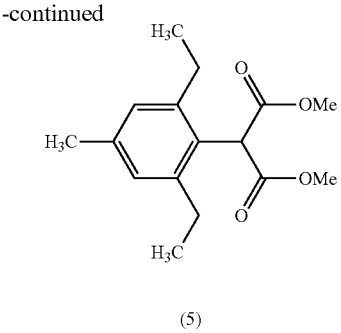

15.2 g of compound (8) obtained in example P6 are hydrogenated at a temperature of 20 to 25° C. with hydrogen using a palladium catalyst (carbon as the carrier, 7 g 5% Pd/C) in 160 ml of tetrahydrofuran. When hydrogenation has ended, the product is filtered through Hyflo and the filtrate obtained is concentrated on a rotary evaporator. 13.7 g of (5) are obtained in the form of yellow crystals with a melting point of 47 to 49° C.

Example P8:

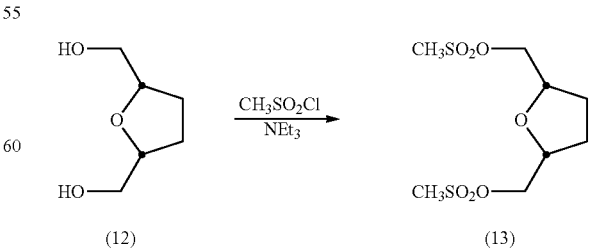

67.8 g (0.59 mols) of methane sulfochloride are added dropwise to a solution, cooled to 0-3° C., of 37.1 g (0.28 mols)

of cis-2,5-bis(hydroxymethyl)tetrahydrofuran (12) and 65.3 g (0.65 mols) of triethylamine in 400 ml of methylene chloride, whereby the temperature is maintained below 7° C. Stirring is subsequently effected over night at a temperature of 20° C. The white suspension thus obtained is added to a suction filter, the residue washed with methylene chloride and the filtrate concentrated by evaporation. The residue is taken up in ethyl acetate, washed with water (2×) and with saturated aqueous sodium chloride solution (1×), dried (Na$_2$SO$_4$) and concentrated. 72.7 g of the dimesylate compound (13) are obtained as a crude oil, which is used in the next reaction without further purification. The educt (12) is known in literature: see e.g. K. Naemura et al., Tetrahedron Asymmetry 1993, 4, 911-918.

Example P9:

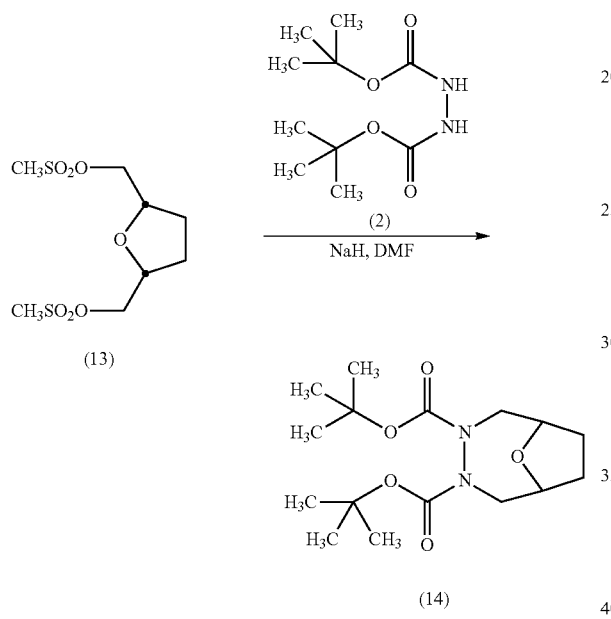

(14) is obtained as a crude brown oil in analogous manner to example P2, from 21.0 g (0.53 mols) of 60% NaH, 58.4 g (0.25 mols) of (2) and 72.5 g (0.25 mols) of dimesylate (13) in a total of 840 ml of dimethylformamide. After purification by chromatography, 53.7 g of pure compound (14) are obtained as a white solid with a melting point of 81 to 83° C.

Example P10:

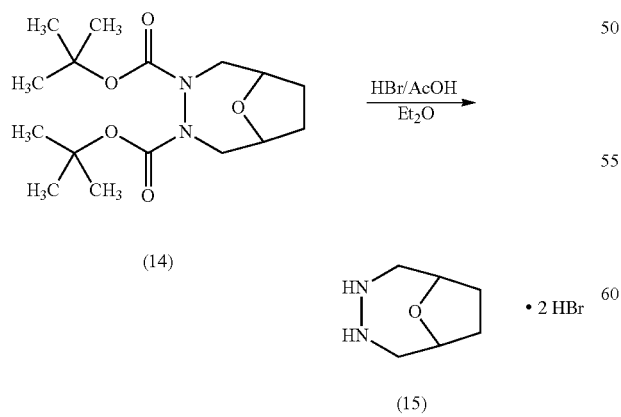

36.5 g of the bicyclic hydrazine (15) are obtained as a solid with a melting point of 262 to 264° C., in analogous manner to example P3, from 53.5 g (0.16 mols) of (14) in 800 ml of diethylether and 90 ml of a 33% solution of hydrogen bromide in conc. acetic acid.

Example P11:

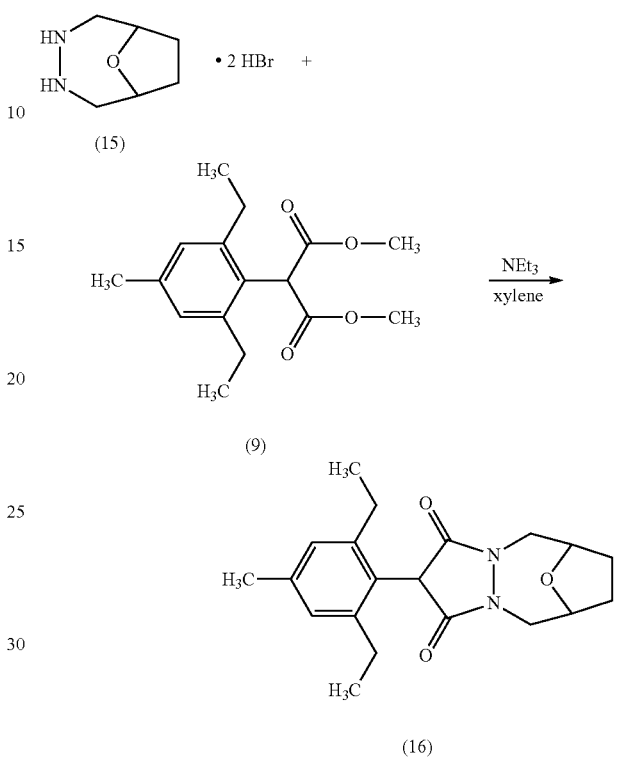

29.7 g of compound (16) are obtained as a solid with a melting point of 287° C., analogously to example P4, from 0.105 mols of the malonate (9) and 30.4 g (0.105 mols) of the hydrazine (15).

Example P12:

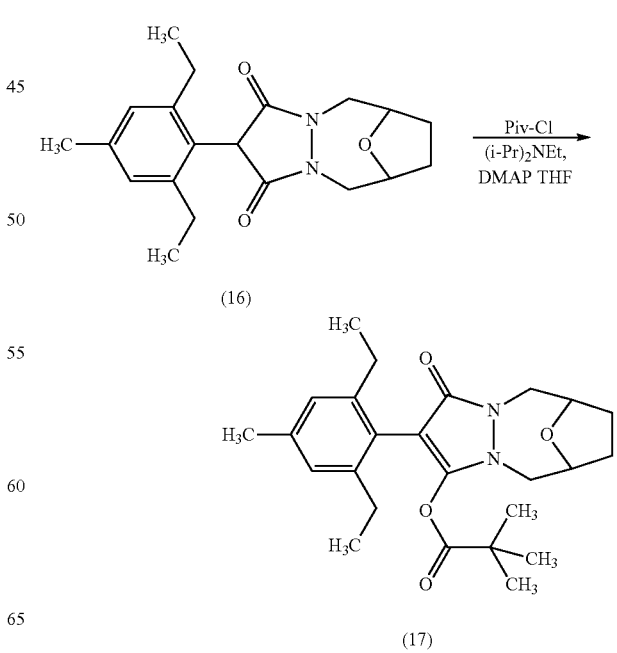

0.83 g of the pivaloyl ester (17) are obtained as a solid with a melting point of 141-143° C., analogously to example P9, from 1.1 g (3.2 mmols) of (16).

If a formula is illustrated for the substituent G, then the left side of this formula is the connection point to the oxygen atom of the heterocycle. The remaining terminal valencies represent methyl groups.

TABLE 1

Compounds of formula Ie:

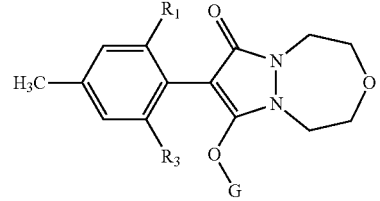

(Ie)

| Comp. No. | $R_1$ | $R_3$ | G | phys. data |
|---|---|---|---|---|
| 1.001 | $CH_3$ | $OCH_3$ | H | |
| 1.002 | $CH_3$ | $OCH_3$ | $C(O)C(CH_3)_3$ | |
| 1.003 | $CH_3$ | $OCH_3$ | $C(O)OCH_2CH_3$ | |
| 1.004 | $CH_2CH_3$ | $CH_3$ | H | m.p. 182-185° C. |
| 1.005 | $CH_2CH_3$ | $CH_3$ | $C(O)C(CH_3)_3$ | m.p. 110-113° C. |
| 1.006 | $CH_2CH_3$ | $CH_3$ | $C(O)OCH_2CH_3$ | |
| 1.007 | $CH_2CH_3$ | $CH_2CH_3$ | H | m.p. 189-191° C. |
| 1.008 | $CH_2CH_3$ | $CH_2CH_3$ | $C(O)C(CH_3)_3$ | m.p. 122-124° C. |
| 1.009 | $CH_2CH_3$ | $CH_2CH_3$ | $C(O)OCH_2CH_3$ | m.p. 114-116° C. |
| 1.010 | $CH=CH_2$ | $CH_3$ | H | m.p. 165-170° C. |
| 1.011 | $CH=CH_2$ | $CH_3$ | $C(O)C(CH_3)_3$ | m.p. 111-113° C. |
| 1.012 | $CH=CH_2$ | $CH_2CH_3$ | H | |
| 1.013 | $CH=CH_2$ | $CH=CH_2$ | H | |
| 1.014 | $CH=CH_2$ | $CH=CH_2$ | $C(O)C(CH_3)_3$ | |
| 1.015 | $C\equiv CH$ | $CH_3$ | H | m.p. 179-184° C. |
| 1.016 | $C\equiv CH$ | $CH_3$ | $C(O)C(CH_3)_3$ | m.p. 109-111° C. |
| 1.017 | $C\equiv CH$ | $CH_3$ | $C(O)OCH_2CH_3$ | |
| 1.018 | $C\equiv CH$ | $CH_2CH_3$ | H | m.p. 189-193° C. |
| 1.019 | $C\equiv CH$ | $CH_2CH_3$ | $C(O)C(CH_3)_3$ | |
| 1.020 | $C\equiv CH$ | $CH_2CH_3$ | $C(O)OCH_2CH_3$ | |
| 1.021 | $C\equiv CH$ | $C\equiv CH$ | H | m.p. 300° C. |
| 1.022 | $C\equiv CH$ | $C\equiv CH$ | $C(O)C(CH_3)_3$ | m.p. 183-185° C. |
| 1.023 | $C\equiv CH$ | $C\equiv CH$ | $C(O)OCH_2CH_3$ | |
| 1.024 | $C\equiv CH$ | $CH=CH_2$ | H | |
| 1.025 | $C\equiv CCH_3$ | $CH_3$ | H | m.p. 179-181° C. |
| 1.026 | $C\equiv CCH_3$ | $CH_3$ | $C(O)C(CH_3)_3$ | m.p. 128-129° C. |
| 1.027 | $C\equiv CCH_3$ | $CH_3$ | $C(O)OCH_2CH_3$ | |
| 1.028 | $C\equiv CCH_3$ | $CH_2CH_3$ | H | |
| 1.029 | $C\equiv CCH_3$ | $CH_2CH_3$ | $C(O)C(CH_3)_3$ | |
| 1.030 | $C\equiv CCH_3$ | $C\equiv CCH_3$ | H | |
| 1.031 | $C\equiv CCH_3$ | $C\equiv CCH_3$ | $C(O)C(CH_3)_3$ | |
| 1.032 | $CH_2CH_2CH_3$ | $CH_3$ | H | m.p. 136-138° C. |
| 1.033 | $CH_2CH_2CH_3$ | $CH_3$ | $C(O)C(CH_3)_3$ | m.p. 65-67° C. |
| 1.034 | $CH_2CH_2CH_3$ | $CH_3$ | $C(O)OCH_2CH_3$ | |
| 1.035 | $CH_2CH_2CH_3$ | $CH_2CH_3$ | H | |
| 1.036 | $CH_2CH_2CH_3$ | $CH_2CH_2CH_3$ | H | |
| 1.037 | $CH_2CH_2CH_3$ | $CH_2CH_2CH_3$ | $C(O)C(CH_3)_3$ | |
| 1.038 | $CH_2CH_2CH_3$ | $CH_2CH_2CH_3$ | $C(O)OCH_2CH_3$ | |
| 1.039 | $CH_2CH_2CH_3$ | $C\equiv CH$ | H | |
| 1.040 | $CH(CH_3)_2$ | $CH_3$ | H | m.p. 214-216° C. |
| 1.041 | $CH(CH_3)_2$ | $CH_3$ | $C(O)C(CH_3)_3$ | m.p. 148-151° C. |
| 1.042 | $CH(CH_3)_2$ | $CH_2CH_3$ | H | |
| 1.043 | $CH(CH_3)_2$ | $C\equiv CH$ | H | |
| 1.044 | cyclopropyl | $CH_3$ | H | |
| 1.045 | cyclopropyl | $CH_2CH_3$ | H | |
| 1.046 | cyclopropyl | $C\equiv CH$ | H | |

TABLE 1-continued

Compounds of formula Ie:

(Ie)

| Comp. No. | R₁ | R₃ | G | phys. data |
|---|---|---|---|---|
| 1.047 | CH₂CH=CH₂ | CH₃ | H | |
| 1.048 | CH₂CH=CH₂ | CH₂CH₃ | H | |
| 1.049 | CH₂CH=CH₂ | C≡CH | H | |
| 1.050 | CH₂CH₂CH₂CH₃ | CH₃ | H | |
| 1.051 | CH₃O— | CH₂CH₃ | H | |
| 1.052 | CH₃O— | CH₂CH₃ | C(O)C(CH₃)₃ | |
| 1.053 | CH₂CH₃ | CH₂CH₃ | SO₂CH(CH₃)₂ | |
| 1.054 | CH₂CH₃ | CH₂CH₃ | SO₂CH₃ | crystalline |
| 1.055 | CH₂CH₃ | CH₂CH₃ | SO₂CH(CH₃)₂ | |
| 1.056 | CH₂CH₃ | CH₂CH₃ | SO₂CF₃ | |
| 1.057 | CH₂CH₃ | CH₂CH₃ | SO₂CH₂CH₃ | |
| 1.058 | CH₂CH₃ | CH₂CH₃ | SO₂CH₂CH(CH₃)₂ | wax |
| 1.059 | CH₂CH₃ | CH₂CH₃ | SO₂CH₂CH₂Cl | |
| 1.060 | CH₂CH₃ | CH₂CH₃ | SO₂CH=CH₂ | wax |
| 1.061 | CH₂CH₃ | CH₂CH₃ | SO₂CH₂CH₂Br | |
| 1.062 | CH₂CH₃ | CH₂CH₃ | (2,1,3-benzoxadiazol-4-ylsulfonyl) | F.: 204-205 |
| 1.063 | CH₂CH₃ | CH₂CH₃ | (2,1,3-benzothiadiazol-4-ylsulfonyl) | F.: 2034-204 |
| 1.064 | CH₂CH₃ | CH₂CH₃ | SO₂-benzyl | F.: 157-158 |
| 1.065 | CH₂CH₃ | CH₂CH₃ | (2-methylallylsulfonyl) | wax |
| 1.066 | CH₂CH₃ | CH₂CH₃ | SO₂CH₂CH₂CH₂Cl | wax |
| 1.067 | CH₂CH₃ | CH₂CH₃ | (2,4-dichlorothien-3-ylsulfonyl) | F.: 126 |
| 1.068 | CH₂CH₃ | CH₂CH₃ | (3,5-dimethylisoxazol-4-ylsulfonyl) | F.: 146 |

TABLE 1-continued

Compounds of formula Ie:

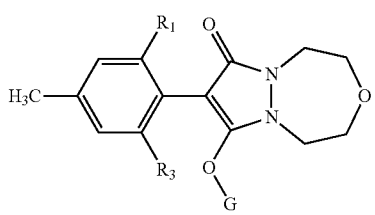

(Ie)

| Comp. No. | R₁ | R₃ | G | phys. data |
|---|---|---|---|---|
| 1.069 | CH₂CH₃ | CH₂CH₃ | 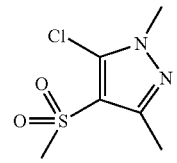 | F.: 82-85 |
| 1.070 | CH₂CH₃ | CH₂CH₃ | SO₂CH₂CH=CH₂ | |
| 1.071 | C≡CH | CH₂CH₃ | SO₂CH₃ | |
| 1.072 | C≡CH | CH₂CH₃ | SO₂CH(CH₃)₂ | |
| 1.073 | C≡CH | CH₂CH₃ | SO₂CH₂CH₂Cl | |
| 1.074 | C≡CH | CH₂CH₃ | SO₂CF₃ | |
| 1.075 | C≡CH | CH₂CH₃ | SO₂CH=CH₂ | |
| 1.076 | C≡CH | OCH₃ | —H | m.p. 202-204 |
| 1.077 | C≡CH | OCH₃ | C(O)C(CH₃)₃ | m.p. 204-206 |
| 1.078 | C≡CSi(CH₃)₃ | OCH₃ | C(O)C(CH₃)₃ | m.p. 169-171 |
| 1.079 | C≡CSi(CH₃)₃ | OCH₃ | —H | m.p. 173-174 |
| 1.080 | Br | OCH₃ | —H | m.p. 217-219 |
| 1.081 | Br | OCH₃ | C(O)C(CH₃)₃ | m.p. 173-175 |
| 1.082 | CH₂CH₃ | CH₂CH₃ | C(O)C(CH₃)₂CH₂CH₃ | m.p. 122-124° C. |
| 1.083 | CH₂CH₃ | CH₂CH₃ | CON(CH₂CH₃)₂ | m.p. 82-84 |
| 1.084 | CH₂CH₃ | C(O)CH₃ | C(O)C(CH₃)₂CH₂CH₃ | m.p. 138-139° C. |
| 1.085 | CH₂CH₃ | C(O)CH₃ | (structure) | |
| 1.086 | CH₂CH₃ | C(O)CH₃ | (structure) | |
| 1.087 | CH₂CH₃ | C(O)CH₃ | (structure) | |
| 1.088 | CH₂CH₃ | C(O)CH₃ | (structure) | |

The invention also relates to a method for the selective control of weeds in crops of cultivated plants, which comprises treating the cultivated plants, the seeds or seedlings or the crop area thereof, with a) a herbicidally effective amount of a herbicide of formula I, b) a herbicidally synergistic amount of at least one herbicide selected from the classes of phenoxy-phenoxypropionic acids, hydroxylamines, sulfonylureas, imidazolinones, pyrimidines, triazines, ureas, PPO, chloroacetanilides, phenoxyacetic acids, triazinones, dinitroanilines, azinones, carbamates, oxyacetamides, thiolcarbamates, azole-ureas, benzoic acids, anilides, nitriles, triones and sulfonamides, as well as the herbicides amitrol, benfuresate, bentazone, cinmethylin, clomazone, chlopyralid, difenzoquat, dithiopyr, ethofumesate, flurochloridone, indanofane, isoxaben, oxaziclomefone, pyridate, pyridafol, quinchlorac, quinmerac, tridiphane, flamprop and glufosinate; and optionally c) to antagonise the herbicide, an antidotally effective amount of a safener selected from cloquintocet, an alkali, alkaline earth, sulfonium or ammonium cation of cloquintocet, cloquintocet-mexyl, mefenpyr, an alkali, alkaline earth, sulfonium or ammonium cation of mefenpyr and mefenpyr-diethyl; and/or d) an additive comprising an oil of vegetable or animal origin, a mineral oil, the alkylesters thereof or mixtures of these oils and oil derivatives.

The cultivated plants which may be protected against the harmful action of the above-mentioned herbicides by the safeners cloquintocet, an alkali, alkaline earth, sulfonium or ammonium cation of cloquintocet, or cloquintocet-mexyl, mefenpyr, an alkali, alkaline earth, sulfonium or ammonium cation of mefenpyr, or mefenpyr-diethyl, are in particular cereals, cotton, soya, sugar beet, sugar cane, plantations, rape, maize and rice, especially maize and cereals. Crops will also be understood to mean those crops that have been made tolerant to herbicides or classes of herbicides by conventional breeding or genetic engineering methods. These are e.g. IMI Maize, Poast Protected Maize (sethoxydim tolerance), Liberty Link Maize, B.t./Liberty Link Maize, IMI/Liberty Link Maize, IMI/Liberty Link /B.t. Maize, Roundup Ready Maize and Roundup Ready/B.t. Maize.

The weeds to be controlled may be both dicot weeds, and preferably monocot weeds, for example the monocot weeds *Avena, Agrostis, Phalaris, Lolium, Bromus, Alopecurus, Setaria, Digitaria Brachiaria, Echinochloa, Panicum, Sorghum hal./bic., Rottboellia, Cyperus, Brachiaria, Echinochloa, Scirpus, Monochoria,* and *Sagittaria* and the dicot weeds *Sinapis, Chenopodium, Stellaria, Galium, Viola, Veronica, Matricaria, Papaver, Solanum Abutilon, Sida, Xanthium, Amaranthus, Ipomoea* and *Chrysanthemum.*

Crop areas will be understood as meaning the areas already under cultivation with the cultivated plants or seeds thereof, as well as the areas intended for cropping with said cultivated plants.

Depending on the end use, a safener according to the invention can be used for pretreating seeds of the crop plants (dressing of seeds or seedlings) or it can be incorporated in the soil before or after sowing. It can, however, also be applied by itself alone or together with the herbicide and the oil additive postemergence. Treatment of the plant or the seeds with the safener can therefore in principle be carried out irrespective of the time of application of the herbicide. Treatment of the plant can, however, also be carried out by simultaneous application of the herbicide, oil additive and safener (e.g. as tank mixture). The concentration of safener with respect to the herbicide will depend substantially on the mode of application. Where a field treatment is carried out either by using a tank mixture with a combination of safener and herbicide or by separate application of safener and herbicide, the ratio of herbicide to safener will usually be from 100:1 to 1:10, preferably 20:1 to 1:1. In field treatment it is usual to apply 0.001 to 1.0 kg/ha, preferably 0.001 to 0.25 kg/ha, of safener.

The concentration of herbicide is usually in the range from 0.001 to 2 kg/ha, but will preferably be from 0.005 to 1 kg/ha.

In the composition of the invention, the compound of formula I is present in relation to the second herbicide in a weight ratio of 1:100 to 1000:1.

In the composition according to the invention, the application rates of oil additive are as a rule between 0.01 and 2% based on the spray mixture. For example, the oil additive can be added to the spray tank in the desired concentration after preparation of the spray mixture.

Preferred oil additives contain mineral oils or an oil of vegetable origin, for example rapeseed oil, olive oil or sunflower oil, alkyl esters of oils of vegetable origin, for example the methyl derivatives, or an oil of animal origin, such as fish oil or beef tallow.

Particularly preferred oil additives contain alkylesters of higher fatty acids ($C_8$-$C_{22}$), especially the methyl derivatives of $C_{12}$-$C_{18}$ fatty acids, for example the methylesters of lauric acid, palmitic acid and oleic acid. These esters are known as methyl laurate (CAS-111-82-0), methyl palmitate (CAS-112-39-0) and methyl oleate (CAS-112-62-9).

The application and efficacy of the oil additives can be improved by combining them with surface-active substances, such as non-ionic, anionic or cationic surfactants. Examples of suitable anionic, non-ionic, and cationic surfactants are listed in WO 97/34485 on pages 7 and 8.

Preferred surface-active substances are anionic surfactants of the dodecylbenzene sulfonate type, especially the calcium salts thereof, as well as non-ionic surfactants of the fatty alcohol ethoxylate type. Especially preferred are ethoxylated $C_{12}$-$C_{22}$-fatty alcohols with a degree of ethoxylation of between 5 and 40. Examples of commercially available, preferred surfactants are the Genapol types (Clariant AG, Muttenz, Switzerland). The concentration of surface-active substances in relation to the total additive is in general between 1 and 30% by weight.

Examples of oil additives, which comprise mixtures of oils or mineral oils, or the derivatives thereof, with surfactants, are Edenor ME SU®, Emery 2231® (Henkel Tochtergesellschaft Cognis GMBH, DE), Turbocharge® (Zeneca Agro, Stoney Creek, Ontario, Calif.) or, most preferably, Actipron® (BP Oil UK Limited, GB).

Furthermore, the addition of an organic solvent to the oil additive/surfactant mixture can effect a further increase in efficacy. Suitable solvents are for example the Solvesso® (ESSO) or Aromatic Solvent® (Exxon Corporation) types. The concentration of such solvents may be from 10 to 80% by weight of the total weight.

Oil additives of this kind, which are also described for example in U.S. Pat. No. 4,834,908, are particularly preferred for the composition according to the invention. A most particularly preferred oil additive is known under the name MERGE® which can be obtained from the BASF Corporation and is basically described for example in U.S. Pat. No. 4,834,908 in column 5, as example COC-1. A further preferred oil additive according to the invention is SCORE® (Novartis Crop Protection Canada).

The compositions of this invention are suitable for all methods of application commonly used in agriculture, including preemergence application, postemergence application and seed dressing.

For seed dressing, 0.001 to 10 g of safener/kg of seeds, preferably 0.05 to 6 g of safener/kg of seeds, is usually applied. If the safener is used in liquid form shortly before sowing to effect soaking, then it is preferred to use safener solutions that contain the active ingredient in a concentration of 1 to 10000 ppm, preferably of 10 to 1000 ppm.

For application, it is preferred to process the safeners according to the invention, or mixtures of the safeners and the herbicides and the oil additives, conveniently together with the customary assistants of formulation technology to formulations, typically to emulsifiable concentrates, coatable pastes, directly sprayable or dilutable solutions, dilute emulsions, wettable powders, soluble powders, dusts, granulates or microcapsules.

Such formulations are described, for example, in WO 97/34485 on pages 9 to 13. The formulations are prepared in known manner, conveniently by homogeneously mixing and/or grinding the active ingredients with liquid or solid formulation assistants, typically solvents or solid carriers. Surface-active compounds (surfactants) may additionally be used for preparing the formulations. Solvents and solid carriers that are suitable for this purpose are described in WO 97/34485 on page 6.

Depending on the herbicide of formula I to be formulated, suitable surface-active compounds are non-ionic, cationic and/or anionic surfactants and surfactant mixtures having good emulsifying, dispersing and wetting properties. Examples of suitable anionic, non-ionic, and cationic surfactants are listed in WO 97/34485 on pages 7 and 8. Also the surfactants customarily for the art of formulation and described, inter alia, in "Mc Cutcheon's Detergents and Emulsifiers Annual" MC Publishing Corp., Ridgewood N.J., 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I-III, Chemical Publishing Co., New York, 1980-81 are suitable for manufacture of the herbicides according to the invention.

The herbicidal compositions will usually contain from 0.1 to 99% by weight, preferably from 0.1 to 95% by weight, of compound mixture of the compound of formula I, the second synergistically active herbicide and optionally the safeners according to the invention, 0 to 2% by weight of the oil additive according to the invention, from 1 to 99.9% by weight of a solid or liquid formulation assistant, and from 0 to 25% by weight, preferably from 0.1 to 25% by weight, of a surfactant. Whereas it is customarily preferred to formulate commercial products as concentrates, the end user will normally use dilute formulations.

The compositions may also contain further ingredients, such as: stabilisers, e.g. where appropriate epoxidised vegetable oils (epoxidised coconut oil, rapeseed oil, or soybean oil); antifoams, typically silicone oil; preservatives; viscosity regulators; binders; tackifiers; as well as fertilisers or other chemical agents. Different methods and techniques may suitably be used for applying the safeners according to the invention or compositions containing them for protecting cultivated plants from the harmful effects of herbicides of formula I, conveniently the following:

i) Seed Dressing a) Dressing the seeds with a wettable powder formulation of the active ingredient of the safeners according to the invention by shaking in a vessel until uniformly distributed on the surface of the seeds (dry treatment), In this instance, approximately 1 to 500 g of active ingredient of the safeners according to the invention (4 g to 2 kg of wettable powder) is used per 100 kg of seeds.

b) Dressing seeds with an emulsifiable concentrate of the safeners according to the invention by method a) (wet treatment).

c) Dressing by immersing the seeds in a mixture containing 100-1000 ppm of safeners according to the invention for 1 to 72 hours and where appropriate subsequently drying them (seed soaking).

In keeping with the natural environment, the preferred method of application is either seed dressing or treatment of the germinated seedlings, because the safener treatment is fully concentrated on the target crop. Usually 1 to 1000 g, preferably 5 to 250 g, of safener is used per 100 kg of seeds. However, depending on the method employed, which also permits the use of other chemical agents or micronutrients, the concentrations may deviate above or below the indicated limit values (repeat dressing).

ii) Application as a Tank Mixture

A liquid formulation of a mixture of safener and herbicide (reciprocal ratio from 20:1 to 1:100) is used, the concentration of herbicide being from 0.005 to 5.0 kg/ha. The oil additive may be added to the tank mixture in an amount of preferably 0.01 to 2% by weight. This tank mixture is applied before or after sowing.

iii) Application in the Furrow

The safener formulated as emulsifiable concentrate, wettable powder or granulate is applied to the open furrow in which the seeds have been sown. After covering the furrow, the herbicide is applied pre-emergence in conventional manner, optionally in combination with the oil additive.

iv) Controlled Release of Compound

A solution of the safener is applied to a mineral granular carrier or to a polymerised granulate (urea/formaldehyde) and then dried. A coating can then be applied (coated granules) that allows the active ingredient to be released at a controlled rate over a specific period of time.

Particularly preferred formulations are made up as follows: %=percent by weight; compound mixture means the mixture of compound of formula I with the synergistically active second herbicide and optionally with the safeners according to the invention and/or the oil additives)

Emulsifiable Concentrates:

| Compound mixture: | 1 to 90%, preferably 5 to 20% |
| surfactant: | 1 to 30%, preferably 10 to 20% |
| liquid carrier: | 5 to 94%, preferably 70 to 85% |

Dusts:

| Compound mixture: | 0.1 to 10%, preferably 0.1 to 5% |
| solid carrier: | 99.9 to 90%, preferably 99.9 to 99% |

Suspension Concentrates:

| Compound mixture: | 5 to 75%, preferably 10 to 50% |
| water: | 94 to 24%, preferably 88 to 30% |
| surfactant: | 1 to 40%, preferably 2 to 30% |

Wettable Powders:

| Compound mixture: | 0.5 to 90%, preferably 1 to 80% |
| surfactant: | 0.5 to 20%, preferably 1 to 15% |
| solid carrier: | 5 to 95%, preferably 15 to 90% |

Granulates:

| Compound mixture: | 0.1 to 30%, preferably 0.1 to 15% |
| solid carrier: | 99.5 to 70%, preferably 97 to 85% |

The invention is illustrated by the following non-limitative Examples.

Formulation Examples for Mixtures of Herbicides and, Where Appropriate, Safeners and Oil Additive (%=Percent by Weight)

| F1. Emulsifiable concentrates | a) | b) | c) | d) |
|---|---|---|---|---|
| compound mixture | 5% | 10% | 25% | 50% |
| calcium dodecylbenzene sulphonate | 6% | 8% | 6% | 8% |
| polyethoxylated castor oil (36 mol EO) | 4% | — | 4% | 4% |
| octylphenol polyglycol ether (7-8 mol EO) | — | 4% | — | 2% |
| cyclohexanone | — | — | 10% | 20% |
| aromatic hydrocarbon mixture $C_9$-$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| compound mixture | 5% | 10% | 50% | 90% |
| 1-methoxy-3-(3-methoxy-propoxy)-propane | — | 20% | 20% | — |
| polyethylene glycol (MW 400) | 20% | 10% | — | — |
| N-Methyl-2-pyrrolidone | — | — | 30% | 10% |
| aromatic hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| compound mixture | 5% | 25% | 50% | 80% |
| sodium ligninsulphonate | 4% | — | 3% | — |
| sodium lauryl sulphate | 2% | 3% | — | 4% |
| sodium diisobutylnaphthalene sulfonate | — | 6% | 5% | 6% |
| octylphenol polyglycol ether (7-8 mol EO) | — | 1% | 2% | — |
| highly dispersed silicic acid | 1% | 3% | 5% | 10% |
| kaolin | 88% | 62% | 35% | — |

The compound is throughly mixed with the adjuvants and this mixture is ground in a suitable mill to give wettable powders which can be diluted with water to give suspensions of any desired concentration.

| F4. Coated granulates | a) | b) | c) |
|---|---|---|---|
| compound mixture | 0.1% | 5% | 15% |
| highly dispersed silicic acid | 0.9% | 2% | 2% |
| Inorganic carrier (Æ 0.1-1 mm) such as $CaCO_3$ or $SiO_2$ | 99.0% | 93% | 83% |

The compound mixture is dissolved in methylene chloride, the solution is sprayed on to the carrier, and the solvent is removed under vacuum.

| F5. Coated granulates | a) | b) | c) |
|---|---|---|---|
| compound mixture | 0.1% | 5% | 15% |
| polyethylene glycol (MW 200) | 1.0% | 2% | 3% |
| highly dispersed silicic acid | 0.9% | 1% | 2% |
| inorganic carrier (Æ 0.1-1 mm) such as $CaCO_3$ or $SiO_2$ | 98.0% | 92% | 80% |

The finely ground active substance is uniformly applied in a mixer to the carrier moistened with polyethylene glycol. Non-dusty coated granulates are obtained in this manner.

| F6. Extruder granulates | a) | b) | c) | d) |
|---|---|---|---|---|
| compound mixture | 0.1% | 3% | 5% | 15% |
| sodium ligninsulphonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. This mixture is extruded and then dried in a stream of air.

| F7. Dusts | a) | b) | c) |
|---|---|---|---|
| compound mixture | 0.1% | 1% | 5% |
| talc | 39.9% | 49% | 35% |
| kaolin | 60.0% | 50% | 60% |

Ready-to-use dusts are obtained by mixing the active ingredient with the carriers and grinding on a suitable mill.

| F8. Suspension concentrates | a) | b) | c) | d) |
|---|---|---|---|---|
| compound mixture | 3% | 10% | 25% | 50% |
| ethylene glycol | 5% | 5% | 5% | 5% |
| nonylphenol polyglycol ether (15 mol EO) | — | 1% | 2% | — |
| sodium ligninsulphonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active substance is intimately mixed with the adjuvants. In this way, a suspension concentrate is obtained from which suspensions of any desired concentration can be prepared by dilution with water.

It is often expedient to formulate herbicides (optionally in combination with the oil additive) and the safeners separately and not to combine them until shortly before application in the applicator in the desired mixing ratio in the form of a "tank mix" in water. The herbicides and the safener may also be formulated individually and combined shortly before application in the applicator in the desired mixing ratio in the form of a "tank mix" in water, and then to add the oil additive.

The selective herbicidal action of the compositions according to the invention is depicted in the following examples.

Biological Examples

Example B1: Postemergence Test:

The test plants are raised in pots under greenhouse conditions until reaching a post-application stage. Standard soil is used as the growing medium. In a post-emergence stage, the herbicides are applied to the test plants both on their own and in a mixture with safeners and/or oil additives, or are applied to crop plants raised from seed previously dressed with safeners. They are applied as an emulsion [prepared from an emulsion concentrate (example F1, c)] of the test substances. The rates of application depend on the optimum dosages determined under field or greenhouse conditions. Evaluation of the tests is made after 2 to 4 weeks (% action=completely dead; 0% action=no phytotoxic action). The oil additive used is ACTIPRON® in a concentration of 0.5% by weight of the spray liquor.

TABLE B1

| | Postemergence herbicidal action on *Alopecurus* | |
|---|---|---|
| Compound mixture | concentration in g/ha | phytotoxic action on *Alopecurus* in % |
| Clodinafop-propargyl + Cloquintocet-mexyl + ACTIPRON ® | 40 + 10 | 40 |

TABLE B1-continued

Postemergence herbicidal action on *Alopecurus*

| Compound mixture | concentration in g/ha | phytotoxic action on *Alopecurus* in % |
|---|---|---|
| comp. no. 1.007 + Cloquintocet-mexyl + ACTIPRON ® | 15 + 3.75 | 0 |
| comp. no. 1.007 + Cloquintocet-mexyl + ACTIPRON ® | 30 + 7.5 | 0 |
| comp. no. 1.007 + Cloquintocet-mexyl + ACTIPRON ® | 45 + 11.25 | 0 |
| comp. no. 1.007 + Cloquintocet-mexyl + ACTIPRON ® | 60 + 15 | 0 |
| comp. no. 1.007 + Cloquintocet-mexyl + ACTIPRON ® | 125 + 31.25 | 40 |
| comp. no. 1.007 + Clodinafop-propargyl + Cloquintocet-mexyl + ACTIPRON ® | 15 + 15 + 3.75 | 92 |
| comp. no. 1.007 + Clodinafop-propargyl + Cloquintocet-mexyl + ACTIPRON ® | 15 + 20 + 5 | 96 |
| comp. no. 1.007 + Clodinafop-propargyl + Cloquintocet-mexyl + ACTIPRON ® | 30 + 15 + 7.5 | 94 |
| comp. no. 1.007 + Clodinafop-propargyl + Cloquintocet-mexyl + ACTIPRON ® | 30 + 20 + 7.5 | 96 |
| comp. no. 1.007 + Clodinafop-propargyl + Cloquintocet-mexyl + ACTIPRON ® | 45 + 15 + 11.25 | 92 |
| comp. no. 1.007 + Clodinafop-propargyl + Cloquintocet-mexyl + ACTIPRON ® | 45 + 20 + 11.25 | 96 |
| comp. no. 1.007 + Clodinafop-propargyl + Cloquintocet-mexyl + ACTIPRON ® | 60 + 15 + 15 | 98 |
| comp. no. 1.007 + Clodinafop-propargyl + Cloquintocet-mexyl + ACTIPRON ® | 60 + 20 + 15 | 99 |

The tests show that the herbicide component Clodinafop-propargyl in combination with the safener Cloquintocet-mexyl and the oil additive ACTIPRON® achieve herbicidal action of only 40% on Alopecurus with a total application rate of herbicide/safener of 40 g/ha. The compound of formula I (no. 1.007) in combination with the safener Cloquintocet-mexyl and the oil additive ACTIPRON® achieve no herbicidal action at all on Alopecurus at 4 tested application rates, and only 40% with the highest application rate (125+31.25 g/ha). Surprisingly, the combination according to the invention of the herbicide of formula I (no. 1.007) with Clodinafop-propargyl, the safener Cloquintocet-mexyl and the oil additive ACTIPRON® is, however, in a position to almost totally eradicate Alopecurus at all the tested application rates (92 to 99% action).

A similar effect is observed if the oil additive MERGE® is used instead of ACTIPRON®.

Example B2: Postemergence Test:

The test plants are raised in pots under greenhouse conditions until reaching a post-application stage. Standard soil is used as the growing medium. In a postemergence stage, the herbicides are applied to the test plants both on their own and in a mixture with safeners and/or oil additives, or are applied to crop plants raised from seed previously dressed with safeners. They are applied as an emulsion [prepared from an emulsion concentrate (example F1, c)] of the test substance. The rates of application depend on the optimum dosages determined under field or greenhouse conditions. Evaluation of the tests is made after 2 to 4 weeks (% action=completely dead; 0% action=no phytotoxic action). The oil additive used is MERGE® in a concentration of 0.7% by weight of the spray liquor.

TABLE B2.1 postemergence herbicidal action on weeds in wheat crops, co-herbicide: Triasulfuron:

| Compound mixture concentration in g/ha | wheat | *Agrostis* | *Avena* | *Lolium* | *Setaria* |
|---|---|---|---|---|---|
| comp. 1.008 (30 g/ha) + Cloquintocet-mexyl (8 g/ha) + Triasulfuron (7 g/ha) | 0 | 80 | 40 | 80 | 50 |
| comp. 1.008 (30 g/ha) + Cloquintocet-mexl (8 g/ha) + MERGE + Triasulfuron (7 g/ha) | 0 | 90 | 100 | 100 | 90 |

TABLE B2.2 postemergence herbicidal action on weeds in wheat crops, co-herbicide: Fenoxaprop-ethyl:

| Compound mixture concentration in g/ha | wheat | *Agrostis* | *Avena* | *Lolium* | *Setaria* |
|---|---|---|---|---|---|
| comp. 1.008 (125 g/ha) + Cloquintocet-mexyl (30 g/ha) + Fenoxaprop-ethyl (1.2 g/ha) | 0 | 100 | 100 | 98 | 98 |
| comp. 1.008 (125 g/ha) + Cloquintocet-mexyl (30 g/ha) + MERGE + Fenoxaprop-ethyl (1.2 g/ha) | 0 | 100 | 100 | 100 | 100 |

TABLE B2.3 postemergence herbicidal action on weeds in wheat crops, co-herbicide: Tralkoxydim:

| Compound mixture concentration in g/ha | wheat | *Agrostis* | *Avena* | *Lolium* | *Setaria* |
|---|---|---|---|---|---|
| comp. 1.008 (30 g/ha) + Cloquintocet-mexyl (8 g/ha) +Tralkoxydim (250 g/ha) | 0 | 98 | 100 | 90 | 80 |
| comp. 1.008 (30 g/ha) + Cloquintocet-mexyl (8 g/ha) +MERGE + Tralkoxydim (250 g/ha) | 0 | 100 | 100 | 100 | 98 |

TABLE B2.4 postemergence herbicidal action on weeds in wheat crops,
co-herbicide: Tralkoxydim:

| Compound mixture concentration in g/ha | wheat | Agrostis | Avena | Lolium | Setaria |
|---|---|---|---|---|---|
| comp. 1.008 (30 g/ha) + Cloquintocet-mexyl (8 g/ha) + Tralkoxydim (125 g/ha) | 0 | 95 | 95 | 80 | 80 |
| comp. 1.008 (30 g/ha) + Cloquintocet-mexyl (8 g/ha) + MERGE + Tralkoxydim (125 g/ha) | 0 | 98 | 98 | 100 | 98 |

From Tables B2.1 to B 2.4, it can be deduced that the addition of the oil additive MERGE® to a mixture of 2 herbicides and one safener leads to a surprising increase in herbicidal action on the weeds without harming the crops.

What is claimed is:

1. A selective herbicidal composition comprising, as the active ingredient a mixture of
   a) a herbicidally effective amount of a compound of formula I

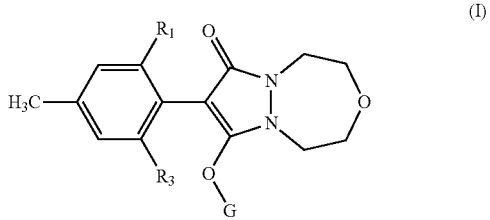

or salts or diastereoisomers thereof, wherein:
   $R_1$ and $R_3$ are $CH_2CH_3$
   G is hydrogen or $C(O)C(CH_3)_3$; and
   b) a herbicidally synergistic amount of at least one herbicide selected from clodinafop-p-propargyl, fenoxaprop-P-ethyl, tralkoxydim, triasulfuron, amidosulfuron, tribenuron, idosulfuron, thifensulfuron-methyl, metsulfuron, flupyrsulfuron, sulfosulfuron, mecoprop, fluroxypyr, MCPA, 2,4-D ester, 2,4-D amine, triallate, prosulfocarb, dicamba, diflufenican, picolinafen, pendimethalin, trifluralin, bromoxynil, ioxynil, flucarbazone, florasulam, propoxycarbazone, and metosulam.

2. Composition according to claim 1, which contains, to antagonise the herbicide, an antidotally effective amount of a safener selected from cloquintocet, an alkali salt of cloquintocet, an alkaline earth salt of cloquintocet, a sulfonium salt of cloquintocet, an ammonium salt of cloquintocet, cloquintocet-mexyl, mefenpyr, an alkali salt of mefenpyr, an alkaline earth salt of mefenpyr, a sulfonium salt of mefenpyr, an ammonium cation salt of mefenpyr and mefenpyrdiethyl.

3. Composition according to claim 1, which contains an additive comprising an oil of vegetable or animal origin, a mineral oil, the alkylesters thereof or mixtures of these oils and oil derivatives.

4. A method of selectively controlling weeds and grasses in crops of cultivated plants, which comprises treating said cultivated plants, the seeds or seedlings or the crop area thereof, with a composition according to claim 1.

5. A method of selectively controlling weeds and grasses in crops of cultivated plants, which comprises treating said cultivated plants, the seeds or seedlings or the crop area thereof, with a composition according to claim 2.

6. A method of selectively controlling weeds and grasses in crops of cultivated plants, which comprises treating said cultivated plants, the seeds or seedlings or the crop area thereof, with a composition according to claim 3.

7. A method according to claim 4 wherein the cultivated plant is cereal or maize.

8. A composition according to claim 1 wherein the at least one herbicide in (b) is selected from clodinafop-p-propargyl and fenoxaprop-P-ethyl.

9. A composition according to claim 1 wherein the at least one herbicide in (b) is tralkoxydim.

10. A composition according to claim 1 wherein the at least one herbicide in (b) is selected from triasulfuron, amidosulfuron, tribenuron, idosulfuron, thifensulfuron-methyl, metsulfuron, flupyrsulfuron, and sulfosulfuron.

11. A composition according to claim 1 wherein the at least one herbicide in (b) is selected from mecoprop, fluroxypyr, MCPA, 2,4-D ester, and 2,4-D amine.

12. A composition according to claim 1 wherein the at least one herbicide in (b) is selected from triallate and prosulfocarb.

13. A composition according to claim 1 wherein the at least one herbicide in (b) is dicamba.

14. A composition according to claim 1 wherein the at least one herbicide in (b) is selected from diflufenican and picolinafen.

15. A composition according to claim 1 wherein the at least one herbicide in (b) is selected from bromoxynil and ioxynil.

16. A composition according to claim 1 wherein the at least one herbicide in (b) is selected from flucarbazone, florasulam, propoxycarbazone, and metosulam.

17. A composition according to claim 1, wherein the at least one herbicide in (b) is selected from pendimethalin and trifluralin.

* * * * *